United States Patent [19]

Nagel

[11] 4,136,253

[45] Jan. 23, 1979

[54] SEMI-SYNTHETIC 4"-SULFONYLAMINO-OLEANDOMYCIN DERIVATIVES

[75] Inventor: Arthur A. Nagel, Gales Ferry, Conn.

[73] Assignee: Pfizer Inc., New York, N.Y.

[21] Appl. No.: 883,608

[22] Filed: Mar. 6, 1978

Related U.S. Application Data

[63] Continuation-in-part of Ser. No. 795,850, May 11, 1977, abandoned.

[51] Int. Cl.$^2$ .................. A61K 31/71; C07H 17/08
[52] U.S. Cl. ........................... 536/9; 424/180; 536/17
[58] Field of Search ..................... 536/9, 17

[56] References Cited

U.S. PATENT DOCUMENTS

| | | | |
|---|---|---|---|
| 3,855,203 | 12/1974 | Hallas et al. | 536/9 |
| 3,983,103 | 9/1976 | Kobrehel et al. | 536/9 |

*Primary Examiner*—Johnnie R. Brown
*Attorney, Agent, or Firm*—Francis X. Murphy; Charles J. Knuth; Albert E. Frost

[57] ABSTRACT

A series of 4"-deoxy-4"-sulfonylamino-oleandomycin antibacterial agents and their preparation from semi-synthetic 4"-deoxy-4"-amino-oleandomycin intermediates.

19 Claims, No Drawings

SEMI-SYNTHETIC 4''-SULFONYLAMINO-OLEANDOMYCIN DERIVATIVES

CROSS-REFERENCE TO RELATED APPLICATIONS

This application is a continuation-in-part of co-pending application Ser. No. 795,850 filed May 11, 1977, and now abandoned.

BACKGROUND OF THE INVENTION

1. Field of the Invention

This invention relates to novel antibacterial agents and, in particular, to a series of 4''-deoxy-4''-sulfonylamino-oleandomycins and their pharmaceutically acceptable acid addition salts.

2. Description of the Prior Art

Oleandomycin, its production in fermentation broths and its use as an antibacterial agent were first described in U.S. Pat. No. 2,757,123. The naturally occurring compound is known to have the following structure:

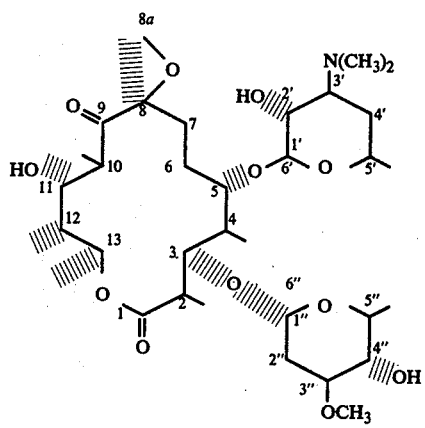

The conventionally accepted numbering scheme and stereochemical representation for oleandomycin and similar compounds is shown at a variety of positions.

U.S. Pat. Nos. 3,884,902 and 3,983,103 claim 4''-erythromycin sulfonate esters and N-sulfonylerythromycylamines, respectively, which have biological profiles different from the compounds claimed in the present invention.

Several synthetic modifications of oleandomycin are known, particularly those in which from one to three of the free hydroxyl groups found at the 2', 4'' and 11-positions are esterified as acetyl esters. In addition, there are described in U.S. Pat. No. 3,022,219 similar modifications in which the acetyl in the above-mentioned esters is replaced with another, preferably unbranched lower alkanoyl of three to six carbon atoms.

SUMMARY OF THE INVENTION

The semi-synthetic oleandomycin antibacterial agents of this invention are of the formulae:

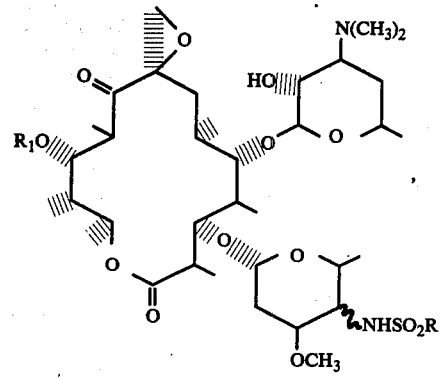

1

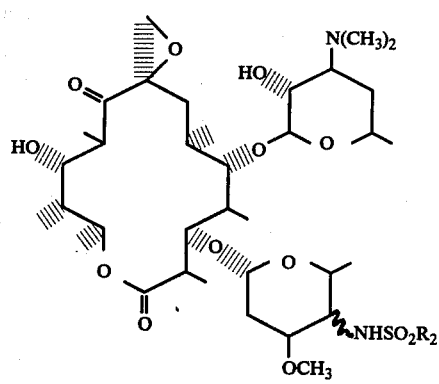

2 and

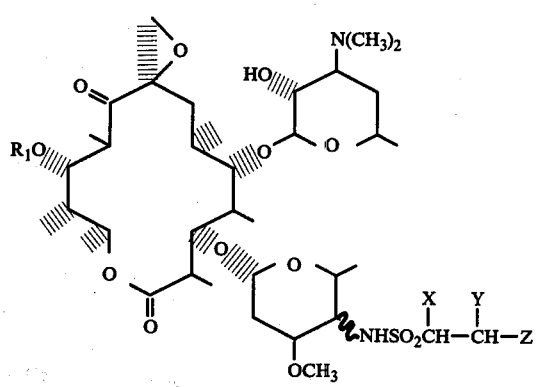

3 and a pharmaceutically acceptable acid addition salt thereof, wherein R is alkyl having from one to three carbon atoms; pyridyl; 1,1,1-trifluoroethyl; phenyl; monosubstituted phenyl wherein said substituent is selected from the group consisting of fluoro, chloro, bromo, iodo, hydroxy, methoxy, cyano, carboxamideo, nitro, amino, carbomethoxy, carbobenzyloxy, carboxy, trifluoromethyl, alkyl having from one to four carbon atoms and acetamido; disubstituted phenyl wherein said substituents are each selected from the group consisting of chloro, nitro, amino, methoxy and methyl; trichlorophenyl; hydroxydichlorophenyl; benzyl; naphthyl; thienyl; chlorothienyl; 2-acetamido-5-thiazolyl; 2-acetamido-4-methyl-5-thiazolyl; 2-benzimidazolyl; dimethyl-2-pyrimidinyl; pyrryl; furyl; monosubstituted thienyl, pyrryl and furyl wherein said substituent is selected from the group consisting of carbomethoxy and alkyl having one to two carbon atoms; or 1-methyl-5-carbomethoxy-3-pyrryl; $R_1$ is alkanoyl having two to three carbon atoms; $R_2$ is phenyl; thienyl; monosubstituted phenyl wherein said substituent is selected from the group consisting of chloro, fluoro, methyl, methoxy and trifluoromethyl; or alkyl substituted thienyl said alkyl having from one to two carbon atoms; X and Y when considered separately are each hydrogen; X and Y when considered together represents a carbon-carbon bond; and Z is hydrogen, bromo, dialkylamino, said alkyl having one to three carbon atoms, alkylthio, said alkyl having from one to three carbon atoms, phenylthio, 2-hydroxyethylthio or 1-morpholino, with the proviso that when X and Y are a carbon-carbon bond, Z is hydrogen.

The amine starting materials leading to the compounds of the present invention are comprised, because of the synthetic method used in their preparation, of two 4"-epimeric amines. Hence, the sulfonamido compounds of the present invention which are formed from said amines are also comprised of an epimeric mixture. Experimentally, it is observed that both epimeric sulfonamides are present in the final product in varying ratios depending on the choice of synthetic method used to prepare the amine intermediate. If the isolated product consists predominantly of one of the epimers, said epimer can be purified by repeated recrystallization from a suitable solvent to a constant melting point. The other epimer, the one present in smaller amounts in the originally isolated solid material, is the predominant product in the mother liquor. It can be recovered therefrom by methods known to those skilled in the art, as for example, the evaporation of the mother liquor and repeated recrystallization of the residue to a product of constant melting point or by chromatography.

Although said mixture of epimers can be separated by methods known to those skilled in the art, for practical reasons it is advantageous to use said mixture as it is isolated from the reaction. However, it is frequently advantageous to purify the mixture of epimers by at least one recrystallization from an appropriate solvent, subjecting it to column chromatography, solvent partitioning or by trituration in an appropriate solvent. Said purification, while not necessarily separating the epimers, removes such extraneous materials as starting materials and undesirable by-products.

The absolute stereochemical assignment for the epimers has not been completed. Both epimers of a given compound, however, exhibit the same type of activity, e.g. as antibacterial agents.

Preferred compounds related to 1 are those wherein R is thienyl and substituted thienyl wherein said substitutent is alkyl having from one to two carbon atoms or carbomethoxy.

Preferred compounds related to 2 comprise those wherein $R_2$ is substituted phenyl, thienyl and alkyl substituted thienyl said alkyl having from one to two carbon atoms.

Preferred compounds related to 3 are those wherein X and Y are each hydrogen and $R_1$ is acetyl.

Preferred among these compounds because of their antibacterial utility are 11-acetyl-4"-deoxy-4"-(2-thienylsulfonylamino)oleandomycin, 11-acetyl-4"-deoxy-4"-(3-thienylsulfonylamino)oleandomycin, 11-acetyl-4"-deoxy-4"-(3-methyl-2-thienylsulfonylamino)oleandomycin, 4"-deoxy-4"-(p-chlorophenylsulfonylamino)oleandomycin, 4"-deoxy-4"-(2-thienylsulfonylamino)oleandomycin, 4"-deoxy-4"-(3-thienylsulfonylamino)oleandomycin, 4"-deoxy-4"-(3-methyl-2-thienylsulfonylamino)oleandomycin, 11-acetyl-4"-deoxy-4"-(2-bromoethylsulfonylamino)oleandomycin, 11-acetyl-4"-deoxy-4"-(2-methylthioethylsulfonylamino)oleandomycin and 11-acetyl-4"-deoxy-4"-(vinylsulfonylamino)oleandomycin.

DETAILED DESCRIPTION OF THE INVENTION

In accordance with the process for synthesizing the 4"-deoxy-4"-sulfonylamino-oleandomycin derived antibacterial agents of formulae 1 and 2, the following scheme, starting with 4"-deoxy-4"-amino-oleandomycin or an 11-alkanoyl derivative thereof, is illustrative.

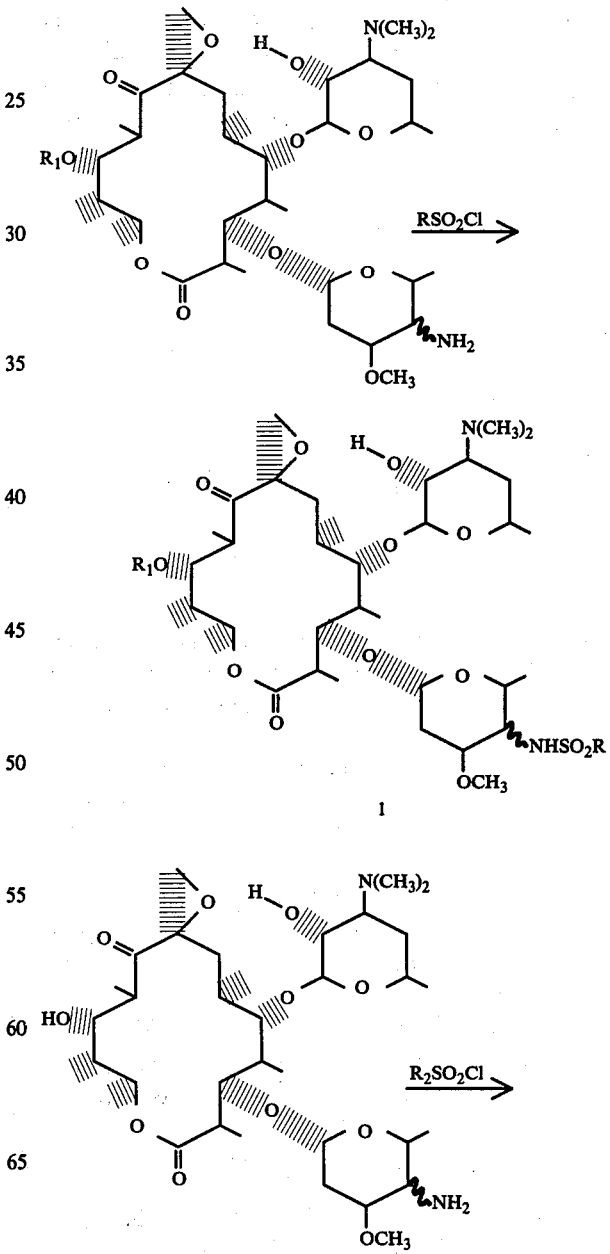

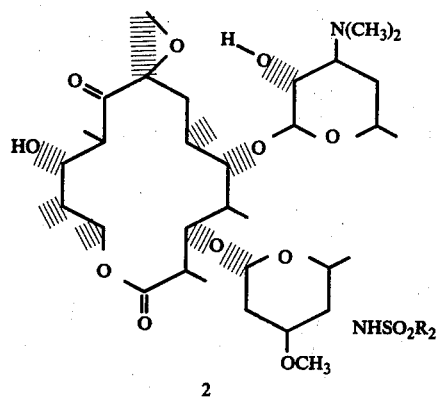

2 wherein R, $R_1$ and $R_2$ are as previously defined.

The above-identified reactions are carried out between a 4″-deoxy-4″-amino-oleandomycin and an appropriate sulfonyl halide in the presence of a acid scavenger in a reaction-inert solvent.

In practice, one mole of the 4″-amino-oleandomycin is contacted with one mole of the sulfonyl halide plus as much as a 2–3% excess of said halide. The acid scavenger, which can be inorganic or organic in nature, is employed to the extent of one mole plus as much as 4–6% excess.

The scavenger can consist of alkali metal or alkaline-earth metal hydroxides, hydrides or carbonates as well as a tertiary organic amine. In addition, secondary amines, such as diisopropyl amine, which are sufficiently hindered such that they do not react with the sulfonyl halide reactant can also be employed. The preferred class of acid scavengers is tertiay amines. Especially preferred within this class is triethylamine.

The reaction-inert solvent used in the aforementioned process should be one which appreciably solubilizes the reactants and does not react to any appreciable extent with either the reactants or the products formed. Preferred are polar solvents which are miscible or immiscible with water. Especially preferred are methylene chloride and acetone-water.

Since heating of amino-oleandomycins leads to some decomposition, it is preferred that the process leading to 1 or 2 be conducted at 0–25° C. Esecially preferred is a reaction conducted at ambient or room temperature.

Reaction time is not critical and is dependent on reaction temperature, concentration and inherent reactivity of the starting reagents. When the reactions are conducted at room temperature at the hereinafter mentioned concentrations, the reaction is essentially complete in 2 to 48 hours.

The reaction, on completion, can be worked-up in one of two manners, both of which are known to those skilled in the art. The first work-up method comprises adding the reaction mixture to water followed by separation of the water immiscible solvent, which contains the desired product, and its subsequent removal to give the crude product. When a water miscible solvent is employed as the reaction-inert solvent, the product is extracted from the water quenched reaction mixture using a water immiscible solvent, such as methylene chloride.

The second method of work-up comprises concentration of the reaction mixture to dryness followed by the extraction of the product from the salt resulting from the scavenger base and hydrogen halide by-product using acetone. The acetone extract can be concentrated to give crude product.

The crude product or an acetone solution thereof is purified by chromatographing on silica gel, a procedure well known in the art, or recrystallization.

The preparation of antibacterial agents of formula 3 wherein X and Y are a carbon-carbon bond and Z is hydrogen are prepared by contacting one mole of the appropriate 11-alkanoyl-4″-deoxy-4″-amino-oleandomycin with two moles of β-bromoethanesulfonyl chloride and four moles of a nonhindered tertiary amine, such as triethylamine.

The reaction temperature is kept at −78° C. for the contacting period and for a one to two hours reaction time.

The solvents appropriate for this process are the same as those employed in the process for preparing compounds 1 and 2 with the further restriction that said solvents do not freeze at the preferred reaction temperature. The preferred solvent is methylene chloride.

The reaction mixture is worked-up in the manner previously described in the process leading to 1 and 2.

In addition to being an antibacterial agent, the 11-alkanoyl-4″-deoxy-4″-(vinylsulfonylamino)oleandomycins prepared by this process are also useful intermediates leading to other antibacterials by a process hereinafter described.

When one mole of the appropriate 11-alkanoyl-4″-deoxy-4″-amino-oleandomycin is contacted with 5–7 moles of β-bromoethanesulfonyl chloride in the presence of 10–12 moles of a hindered amine, such as 2,6-lutidine, at about −4 to 0° C. in a reaction-inert solvent there is obtained the corresponding 11-alkanoyl-4″-deoxy-4″-(β-bromoethylsulfonylamino)oleandomycin (X,Y═H; Z═Br).

At a reaction temperature of about 0° C. a reaction time of 1–2 hours is preferred. The preferred solvent at these reaction temperatures is methylene chloride.

The product is obtained and purified by a procedure similar to that described for the synthesis of compounds 1 and 2.

The remaining compounds represented by formula 3 are prepared by a Micheal Addition of the appropriate amine or mercaptan to the requisite 11-alkanoyl-4″-deoxy-4″-(vinylsulfonylamino)oleandomycin, shown as follows:

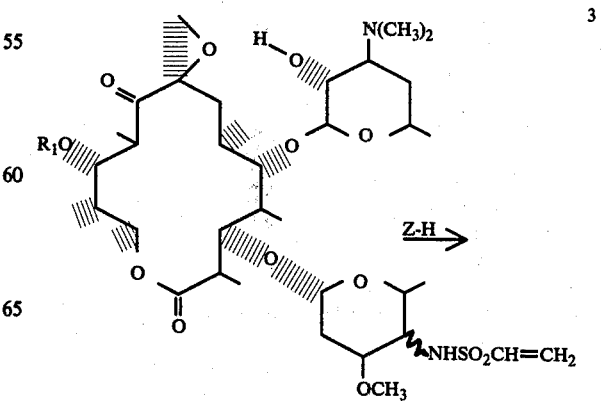

3

-continued

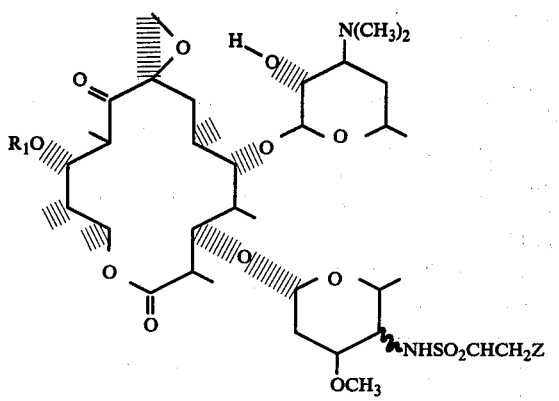

In practice, the vinylsulfonylamino compound is contacted with a three to ten fold molar excess of the amine or mercaptan in a reaction-inert solvent, at ambient temperatures for 12-48 hours. The solvent should meet the same requirements as aforementioned in the synthesis of 1 and 2. The preferred solvent is benzene.

When a mercaptan is employed as one of the reactants, an inorganic or tertiary amine base is used to facilitate the reaction. It is preferred that a molar quantity of base, at least equal to the vinylsulfonylamino compound, be employed. The preferred base is potassium carbonate.

On completion of the reaction the product is obtained by either removal of the solvent and excess reactant under reduced pressure, or by quenching the reaction in water followed by separating of the organic phase and concentrating to dryness.

The starting 4"-amino compounds used in the synthesis of antibacterial agents of the present invention are synthesized by oxidation of the natural oleandomycin followed by a reductive amination of the resultant ketone as hereinafter described.

In the utilization of the chemotherapeutic activity of those compounds of the present invention which form salts, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt with a suitable base or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic, gluconic, aspartic, glutamic, pyroglutamic and lauryl sulfuric acids.

The novel 4"-deoxy-4"-amino-oleandomycin derivatives described herein exhibit in vitro activity against a variety of Gram-positive microorganisms such as Staphylococcus aureus and Streptococcus pyogenes and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sick-room utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvent, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive microorganisms via the oral and/or parenteral route of administration in animals, including man. Their in vivo activity is more limited as regards susceptible organisms and is determined by the usual procedure which comprises inoculating mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 1 mg./kg. to about 200 mg./kg. of body weight per day. The favored dosage range is from about 2 mg./kg. to about 100 mg./kg. of body weight per day and the preferred range from about 2 mg./kg. to about 50 mg./kg. of body weight per day. Vehicles suitable for parenteral injection may be either aqueous such as water, isotonic saline, isotonic dextrose, Ringers' solution, or non-aqueous such as fatty oils or vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The following examples are provided solely for the purpose of illustration and are not to be construed as limitations of this invention, many variations of which are possible without departing from the spirit or scope thereof.

EXAMPLE 1

11-Acetyl-4''-deoxy-4''-(2-thienylsulfonylamino)oleandomycin

To 30 ml. of dry methylene chloride is added 2.9 g. (4.0 mmoles) of 11-acetyl-4''-deoxy-4''-amino-oleandomycin, 740 mg. (4.1 mmoles) of 2-thienylsulfonyl chloride and 0.58 ml. (4.2 mmoles) of triethylamine, and the resulting reaction mixture allowed to stir at room temperature for 18 hrs. The reaction mixture is poured into 50 ml. of water and is subsequently washed with a saturated brine solution and dried over sodium sulfate. The solvent is removed under reduced pressure and the residual foam purified by chromatographing over a silica gel column using acetone as the solvent and eluate. The fractions containing the product are combined and concentrated in vacuo to dryness, 1.3 g.

NMR ($\delta$, CDCl$_3$): 2.03 (3H)s; 2.30 (6H)s; 2.63 (2H)d; 3.16 (3H)s and 6.8–7.8 (3H)m.

EXAMPLE 2

Starting with 11-acetyl-4''-deoxy-4''-amino-oleandomycin and the appropriate sulfonyl chloride and employing the procedure of Example 1, the following compounds are prepared:

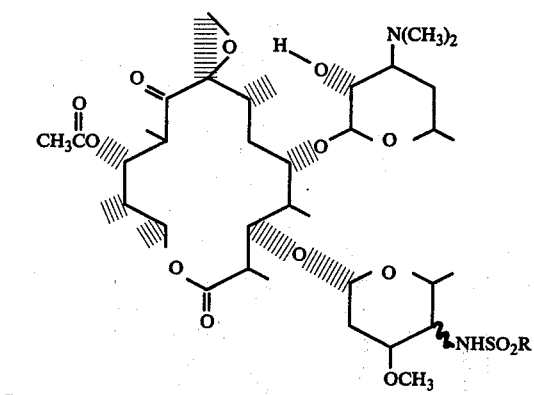

| R | NMR ($\delta$, CDCl$_3$) |
|---|---|
| Cl-thienyl | 2.08 (3H)s; 2.30 (6H)s; 2.67 (2H)m; 3.23 (3H)s and 6.87 and 7.45 (2H)s. |
| CH$_3$CNH-thiazolyl-CH$_3$ | 2.09 (3H)s; 2.42 (6H)s; 2.70 (2H)m and 3.26 (3H)s. |
| CH$_3$CNH-thiazolyl | 2.0 (3H)s; 2.33 (6H)s; 2.40 (3H)s; 2.66 (2H)d; 3.33 (3H)s and 7.86 (1H)s. |
| pyridyl | 2.03 (3H)s; 2.33 (6H)s; 2.66 (2H)d; 3.03 (3H)s and 7.40–9.16 (4H)m. |
| benzimidazolyl | 2.06 (3H)s; 2.36 (6H)s; 2.71 (2H)s; 3.28 (3H)s and 7.36–7.56 and 7.66–7.92 (4H)m. |

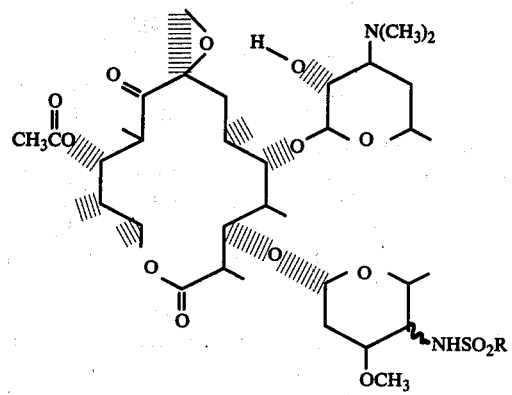

| R | NMR ($\delta$, CDCl$_3$) |
|---|---|
| pyrimidinyl dimethyl | 2.08 (3H)s; 2.31 (6H)s; 2.59 (6H)s; 2.65 (2H)s; 3.01 (3H)s and 7.11 (1)s. |
| thienyl | 2.07 (3H)s; 2.32 (6H)s; 2.67 (2H)s; 3.20 (3H)s; 7.32 (1H)m; 7.43 (1H)m and 8.02 (1H)m. |
| pyrrolyl | 2.06 (3H)s; 2.29 (6H)s; 2.64 (2H)m; 3.26 (3H)s; 6.52 (1H)m; 6.77 (1H)m and 7.29 (1H)m. |
| CH$_3$O$_2$C-pyrrolyl-CH$_3$ | 2.07 (3H)s; 2.62 (6H)s; 3.25 (3H)s; 3.83 (3H)s; 3.95 (3H)s and 7.30 (2H)m. |
| furyl | 2.08 (3H)s; 2.31 (6H)s; 2.68 (2H)m; 3.25 (3H)s; 6.74 (1H)m; 7.48 (1H)m and 8.00 (1H)m. |

EXAMPLE 3

The procedure of Example 1 is repeated, starting with the requisite sulfonyl chloride and 11-alkanoyl-4''-deoxy-4''-amino-oleandomycin, to give the following congeners: 11-propionyl-4''-deoxy-4''-(2-thienylsulfonylamino)oleandomycin; 11-propionyl-4''-deoxy-4''-(2-acetamido-5-thiazolylsulfonylamino)oleandomycin; 11-propionyl-4''-deoxy-4''-(2-benzimidazolylsulfonylamino)oleandomycin; 11-acetyl-4''-deoxy-4''-(4,5-dimethyl-2-pyrimidinylsulfonylamino)oleandomycin; 11-propionyl-4''-deoxy-4''-(4,6-dimethyl-2-pyrimidinylsulfonylamino)oleandomycin; 11-propionyl-4''-deoxy-4''-(3-chloro-2-thienylsulfonylamino)oleandomycin; 11-acetyl-4''-deoxy-4''-(4-chloro-2-thienylsulfonylamino)oleandomycin; 11-acetyl-4''-deoxy-4''-(2-chloro-4-thienylsulfonylamino)oleandomycin; 11-acetyl-4''-deoxy-4''-(2-pyridylsulfonylamino)oleandomycin; 11-propionyl-4''-deoxy-4''-(3-pyridylsulfonylamino)oleandomycin; 11-acetyl-4''-deoxy-4''-(4-pyridylsulfonylamino)oleandomycin; 11-acetyl-4''-deoxy-4''-(2-furylsulfonylamino)oleandomycin; 11-propionyl-4''-deoxy-4''-(2-pyrrylsulfonylamino)oleandomycin; 11-propionyl-4''-deoxy-4''-(1-methyl-5-carbomethoxy-3-pyrrylsulfonylamino)oleandomycin; and 11-propionyl-4''-deoxy-4''-(3-thienylsulfonylamino)oleandomycin.

EXAMPLE 4

11-Acetyl-4″-deoxy-4″-(p-chlorophenylsulfonylamino)oleandomycin

To a solution of 2.91 g. (4.0 mmoles) of 11-acetyl-4″-deoxy-4″-amino-oleandomycin and 528 μl (4.2 mmoles) of triethylamine in 20 ml. of methylene chloride is added in portions 865 mg. (4.1 mmoles) of p-chlorophenylsulfonyl chloride, and the resulting reaction mixture allowed to stir at room temperature overnight. The reaction is concentrated to dryness in vacuo and the residue treated with 10 ml. of acetone. The suspension is filtered and the filtrate chromatographed on 160 g. of silica gel using acetone as eluate. Fractions 51 through 63 comprising 10 ml. each are collected and concentrated under reduced pressure to give 857 mg. of the pure product. Fractions 42–52 and 64–92 yielded 1.21 g. of less pure product.

NMR (δ, CDCl₃): 2.13 (3H)s; 2.36 (6H)s; 2.73 (2H)d; 3.13 (3H)s and 7.3–8.2 (4H)q.

Similarly, 20 g. of 11-acetyl-4″-deoxy-4″-amino-oleandomycin, 7.24 g. of p-chlorophenylsulfonyl chloride and 5.36 g. of triethylamine in a solvent system comprising 350 ml. of acetone and 350 ml. of water gave 17.1 g. of the desired product which crystallized from the reaction mixture, m.p. 202°–203.5° C. The analytical sample is recrystallized from ethanol water.

EXAMPLE 5

Employing the procedure of Example 4 and starting with the requisite sulfonyl chloride and 11-acetyl-4″-deoxy-4″-amino-oleandomycin, the following compounds are prepared:

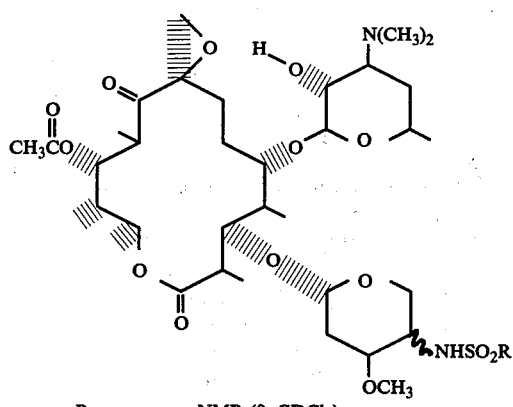

| R | NMR (δ, CDCl₃) |
|---|---|
| I—⟨⟩— | 2.08 (3H)s; 2.33(6H)s; 2.70 (2H)d; 3.11 (3H)s; and 7.5–8.2 (4H)q. |
| F—⟨⟩— | 2.08 (3H)s; 2.31 (6H)s; 2.66 (2H)d; 3.06 (3H)s and 7.0–8.4 (4H)m. |
| Cl—⟨⟩— | 2.03 (3H)s; 2.33 (6H)s; 2.66 (2H)d; 3.10 (3H)s; and 7.3–8.0 (4H)m. |

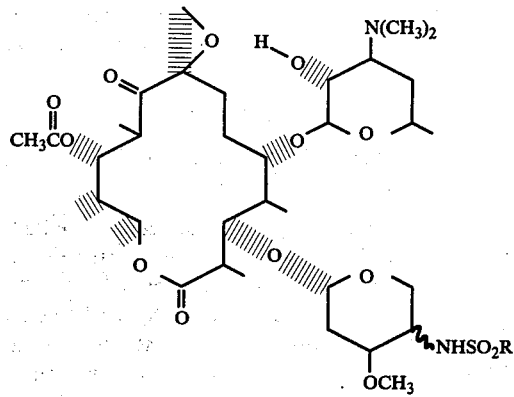

| R | NMR (δ, CDCl₃) |
|---|---|
| ⟨⟩—Cl | 2.03 (3H)s; 2.33 (6H)s; 2.63 (2H)d; 3.23 (3H)s and 7.2–8.4 (4H)m. |
| ⟨⟩—F | 2.13 (3H)s; 2.35 (6H)s; 2.70 (2H)d; 2.90 (3H)s and 7.0–8.2 (4H)m. |
| Br—⟨⟩— | 2.10 (3H)s; 2.33 (6H)s; 2.66 (2H)d; 3.10 (3H)s and 7.5–7.93 (4H)m. |

EXAMPLE 6

The procedure of Example 4 is again repeated starting with the appropriate sulfonyl chloride and 11-alkanoyl-4″-deoxy-4″-amino-oleandomycin to give the following products: 11-propionyl-4″-deoxy-4″-(p-chlorophenylsulfonylamino)oleandomycin; 11-acetyl-4″-deoxy-4″-(m-bromophenylsulfonylamino)oleandomycin; 11-acetyl-4″-deoxy-4″-(m-fluorophenylsulfonylamino)oleandomycin; 11-propionyl-4″-deoxy-4″-(m-iodophenylsulfonylamino)oleandomycin; 11-propionyl-4″-deoxy-4″-(p-fluorophenylsulfonylamino)oleandomycin; 11-propionyl-4″-deoxy-4″-(p-bromophenylsulfonylamino)oleandomycin; 11-acetyl-4″-deoxy-4″-(m-iodophenylsulfonylamino)oleandomycin and 11-acetyl-4″-deoxy-4″-(o-bromophenylsulfonylamino)oleandomycin.

EXAMPLE 7

11-Acetyl-4″-deoxy-4″-(o-tolylsulfonylamino)oleandomycin

A solution of 2.9 g. (4.0 mmoles) of 11-acetyl-4″-deoxy-4″-amino-oleandomycin, 780 mg. (4.1 mmoles) of o-tolylsulfonyl chloride and 0.58 ml. (4.2 mmoles) of triethylamine in 30 ml. of methylene chloride is allowed to stir at room temperature for 48 hrs. The reaction is quenched in 50 ml. of water and the separated organic layer washed with a saturated brine solution and dried over sodium sulfate. The solvent is removed in vacuo and the residual yellow foam chromatographed on 200 g. of silica gel in a 3 cm. diameter column. The product is eluted from the column with acetone collected in 10 ml. fractions. Those fractions containing the pure product, as assayed by thin-layer chromatography, are combined and concentrated to dryness under reduced pressure to give 1.3 g.

NMR (δ, CDCl$_3$): 2.06 (3H)s; 2.33 (6H)s; 2.46 (2H)d; 2.73 (3H)s and 7.1–8.2 (4H)m.

EXAMPLE 8

The procedure of Example 7 is repeated, starting with the appropriate sulfonyl chloride and 11-acetyl-4''-deoxy-4''-amino-oleandomycin, to give the following compounds:

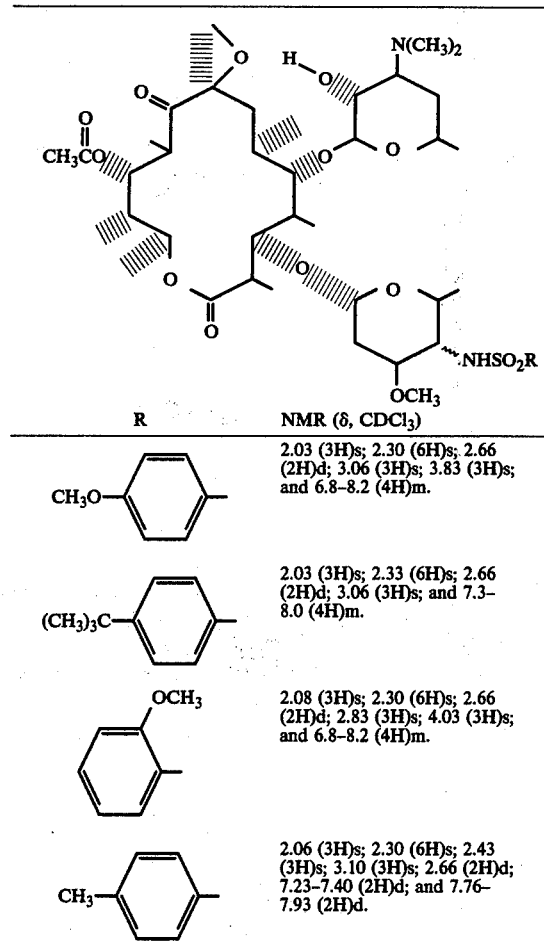

| R | NMR (δ, CDCl$_3$) |
|---|---|
| CH$_3$O—⌬— | 2.03 (3H)s; 2.30 (6H)s; 2.66 (2H)d; 3.06 (3H)s; 3.83 (3H)s; and 6.8–8.2 (4H)m. |
| (CH$_3$)$_3$C—⌬— | 2.03 (3H)s; 2.33 (6H)s; 2.66 (2H)d; 3.06 (3H)s; and 7.3–8.0 (4H)m. |
| OCH$_3$ ⌬— | 2.08 (3H)s; 2.30 (6H)s; 2.66 (2H)d; 2.83 (3H)s; 4.03 (3H)s; and 6.8–8.2 (4H)m. |
| CH$_3$—⌬— | 2.06 (3H)s; 2.30 (6H)s; 2.43 (3H)s; 3.10 (3H)s; 2.66 (2H)d; 7.23–7.40 (2H)d; and 7.76–7.93 (2H)d. |

EXAMPLE 9

Starting with the appropriate 11-alkanoyl-4''-deoxy-4''-amino-oleandomycin and sulfonyl chloride and employing the procedure of Example 7, the following analogs are synthesized: 11-acetyl-4''-deoxy-4''-(m-tolylsulfonylamino)oleandomycin; 11-propionyl-4''-deoxy-4''-(p-methoxyphenylsulfonylamino)oleandomycin; 11-acetyl-4''-deoxy-4''-(m-methoxyphenylsulfonylamino)oleandomycin; 11-propionyl-4''-deoxy-4''-(p-tolylsulfonylamino)oleandomycin; 11-acetyl-4''-deoxy-4''-(p-isopropylphenylsulfonylamino)oleandomycin; 11-acetyl-4''-deoxy-4''-(o-ethylphenylsulfonylamino)oleandomycin; 11-propionyl-4''-deoxy-4''-(o-[n-propyl]phenylsulfonylamino)oleandomycin; 11-acetyl-4''-deoxy-4''-(p-[s-butyl]phenylsulfonylamino)oleandomycin; and 11-propionyl-4''deoxy-4''-(p-[n-butyl]phenylsulfonylamino)oleandomycin.

EXAMPLE 10

11-Acetyl-4''-deoxy-4''-phenylsulfonylamino-oleandomycin

To a solution of 2.91 g. (4.0 mmoles) of 11-acetyl-4''-deoxy-4''-amino-oleandomycin and 424 mg. (4.2 mmoles) of triethylamine in 30 ml. of methylene chloride and cool in an ice bath is added 722 mg. (4.1 mmoles) of benzenesulfonyl chloride. After 10 min., the bath is removed and the reaction mixture allowed to stir at room temperature overnight. The reaction is quenched with 50 ml. of water and the organic layer washed with a saturated brine solution and dried over sodium sulfate. Removal of the solvent provides the crude product which is further purified by chromatographing over 160 g. of silica gel using acetone as the eluate. Cuts (10 ml. each) 61–93, which contain the pure product as determined by thin-layer chromatography, are combined and concentrated to dry under reduced pressure to give 1.5 g. of the desired product.

NMR (δ, CDCl$_3$): 2.06 (3H)s; 2.30 (6H)s; 2.63 (2H)d; 3.06 (3H)s; and 7.3–8.2 (5H)m.

Also prepared by the procedure of Example 10 when the appropriate starting materials are employed are:

11-acetyl-4''-deoxy-4''-(2-naphthylsulfonylamino)oleandomycin

NMR (δ, CDCl$_3$): 2.03 (3H)s; 2.26 (6H)s; 2.65 (2H)d; 2.96 (3H); and 7.4–8.6 (7H)m; and cl 11-acetyl-4''-deoxy-4''-benzylsulfonylamino-oleandomycin NMR (δ, CDCl$_3$): 2.00 (3H)s; 2.30 (6H)s; 2.63 (2H)d; 3.46 (3H)s; 4.33 (2H)s; and 7.36 (5H)s.

EXAMPLE 11

11-Acetyl-4''-deoxy-4''-(p-benzyloxycarbonylphenylsulfonylamino)oleandomycin

A solution of 2.55 g. (3.5 mmoles) of 11-acetyl-4''-deoxy-4''-amino-oleandomycin, 1.12 g. (3.6 mmoles) of p-benzyloxycarbonylphenylsulfonyl chloride and 379 mg. (3.75 mmoles) of triethylamine in 25 ml. of methylene chloride is allowed to stir at room temperature overnight. The solvent is removed in vacuo and the residue triturated in 10 ml. of acetone. The solids are filtered and the filtrate chromatographed on 280 g. of silica gel using acetone as the eluate and fraction sizes of 10 ml. Fractions 90–203, which by thin-layer chromatography contain most of the pure product, are combined and concentrated under reduced pressure to give 1.25 g. of the desired product.

NMR (δ, CDCl$_3$): 2.04 (3H)s; 2.30 (6H)s; 2.66 (2H)d; 3.01 (3H)s; 5.48 (2H)s; 7.50 (5H)s; and 8.03–8.53 (4H)m.

EXAMPLE 12

Starting with the appropriate sulfonyl chloride and 11-acetyl-4''-deoxy-4''-amino-oleandomycin and employing the procedure of Example 11 gives the following compounds:

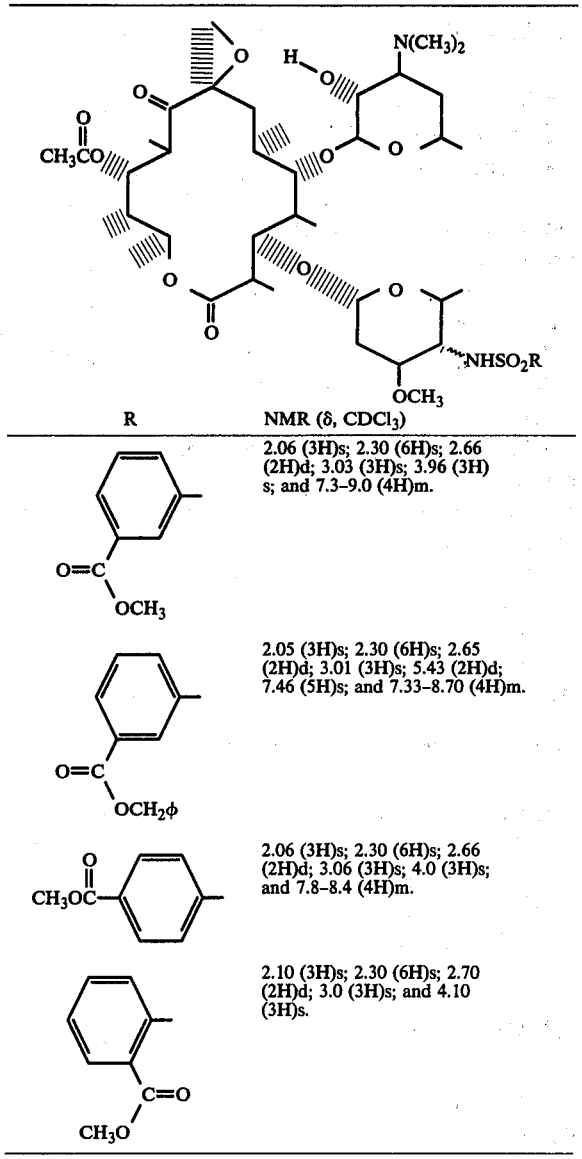

| R | NMR (δ, CDCl₃) |
|---|---|
| *3-methoxycarbonylphenyl* (O=C(OCH₃) at meta) | 2.06 (3H)s; 2.30 (6H)s; 2.66 (2H)d; 3.03 (3H)s; 3.96 (3H)s; and 7.3–9.0 (4H)m. |
| *3-benzyloxycarbonylphenyl* (O=C(OCH₂φ) at meta) | 2.05 (3H)s; 2.30 (6H)s; 2.65 (2H)d; 3.01 (3H)s; 5.43 (2H)d; 7.46 (5H)s; and 7.33–8.70 (4H)m. |
| *4-acetylphenyl* (CH₃OC(=O)– para) | 2.06 (3H)s; 2.30 (6H)s; 2.66 (2H)d; 3.06 (3H)s; 4.0 (3H)s; and 7.8–8.4 (4H)m. |
| *2-methoxycarbonylphenyl* (C=O/OCH₃ at ortho) | 2.10 (3H)s; 2.30 (6H)s; 2.70 (2H)d; 3.0 (3H)s; and 4.10 (3H)s. |

EXAMPLE 13

The procedure of Example 11 is again repeated, starting with the requisite 11-alkanoyl-4"-deoxy-4"-amino-oleandomycin and sulfonyl chloride to give the following compounds: 11-acetyl-4"-deoxy-4"-(o-benzyloxycarbonylphenylsulfonylamino)oleandomycin; 11-propionyl-4"-deoxy-4"-(p-methoxycarbonylphenylsulfonylamino)oleandomycin; 11-propionyl-4"-deoxy-4"-(m-benzyloxycarbonylphenylsulfonylamino)oleandomycin; 11-propionyl-4"-deoxy-4"-(p-benzyloxycarbonylphenylsulfonylamino)oleandomycin; 11-propionyl-4"-deoxy-4"-(o-methoxycarbonylphenylsulfonylamino)oleandomycin; and 11-propionyl-4"-deoxy-4"-(o-benzyloxycarbonylphenylsulfonylamino)oleandomycin.

EXAMPLE 14

11-Acetyl-4"-deoxy-4"-(p-carboxyphenylsulfonylamino)oleandomycin

A suspension of 400 mg. of 10% palladium-on-charcoal in 40 ml. of ethyl acetate containing 800 mg. of 11-acetyl-4"-deoxy-4"-(p-benzyloxycarbonylphenylsulfonylamino)oleandomycin is shaken in a hydrogen atmosphere at an initial pressure of 50 p.s.i. at room temperature for 2 hrs. An additional 250 mg. of catalyst is added and the reaction continued for 2 hrs. The spent catalyst is filtered and the solvent removed in vacuo to give 450 mg. of the desired product.

NMR (δ, CDCl₃): 2.06 (3H)s; 2.86 (6H)s; 2.68 (2H)d; 3.30 (3H)s; and 7.5–8.4 (4H)m.

EXAMPLE 15

Starting with the appropriate 11-alkanoyl-4"-deoxy-4"-(benzyloxycarbonylphenylsulfonylamino)oleandomycin described in Example 12 and 13 and employing the procedure of Example 14, the following compounds are prepared: 11-acetyl-4"-deoxy-4"-(m-carboxyphenylsulfonylamino)oleandomycin; 11-acetyl-4"-deoxy-4"-(o-carboxyphenylsulfonylamino)oleandomycin; 11-propionyl-4"-deoxy-4"-(m-carboxyphenylsulfonylamino)oleandomycin; 11-propionyl-4"-deoxy-4"-(p-carboxyphenylsulfonylamino)oleandomycin; and 11-propionyl-4"-deoxy-4"-(o-carboxyphenylsulfonylamino)oleandomycin.

EXAMPLE 16

11-Acetyl-4"-deoxy-4"-(o-nitrophenylsulfonylamino)oleandomycin

Five grams (6.8 moles) of 11-acetyl-4"-deoxy-4"-amino-oleandomycin, 1.5 g. (7.0 mmoles) of o-nitrobenzenesulfonyl chloride and 0.98 ml. of triethylamine are combined in 50 ml. of methylene chloride and allowed to stir at room temperature for 48 hrs. The reaction mixture is quenched with an equal volume of water, and the organic phase washed with a saturated brine solution and dried over sodium sulfate. Removal of the solvent under reduced pressure provides the crude product as a foam. The product is purified by chromatographing on 140 g. of silica gel in a 3 cm. diameter column using acetone as the eluate. Fractions 20–30, comprising 50 ml. each, are collected, combined and concentrated to dryness to give 3.4 g. of the desired compound.

NMR (δ, CDCl₃): 2.10 (3H)s; 2.33 (6H)s; 4.36 (2H)d; 2.90 (3H)s; and 7.4–8.4 (4H)m.

Similarly, when the proper starting materials are employed and the above procedure is repeated the following compounds are prepared:

11-acetyl-4"-deoxy-4"-(m-nitrophenylsulfonylamino)oleandomycin

NMR (δ, CDCl₃): 2.06 (3H)s; 2.30 (6H)s; 2.66 (2H)d; 3.06 (3H)s; and 7.4–9.0 m and 11-acetyl-4"-deoxy-4"-(p-nitrophenylsulfonylamino)oleandomycin NMR (δ, CDCl₃): 2.10 (3H)s; 2.35 (6H)s; 2.68 (2H)d; 3.06 (3H)s; and 8.0–8.6 (4H)m.

EXAMPLE 17

11-Acetyl-4"-deoxy-4"-(p-hydroxyphenylsulfonylamino)oleandomycin

A solution of 2.55 g. (3.5 mmoles) of 11-acetyl-4"-deoxy-4"-amino-oleandomycin, 701 mg. (3.65 moles) of p-hydroxyphenylsulfonyl chloride and 51.8 μl. in 25 ml. of methylene chloride is allowed to stir at room temperature for 48 hours. The solvent is removed in vacuo and the residue treated with 10 ml. of acetone. The insolubles are filtered and the filtrate chromatographed over 200 g. of silica gel using acetone as the eluate. Fractions 116–175, which by thin-layer chromatography contains the pure product, are combined and concentrated to dryness under reduced pressure to give 550 mg. of the desired product.

NMR (δ, CDCl$_3$): 2.0 (3H)s; 2.33 (6H)s; 2.68 (2H)d; 3.06 (3H); and 6.6–8.0 (4H)m. EXAMPLE 18

Starting with the requisite 11-alkanoyl-4″-deoxy-4″-amino-oleandomycin and sulfonyl chloride and employing the procedure of Example 17, the following compounds are prepared: 11-acetyl-4″-deoxy-4″-(m-hydroxyphenylsulfonylamino)-oleandomycin; 11-propionyl-4″-deoxy-4″-(p-hydroxyphenylsulfonylamino)oleandomycin; 11-propionyl-4″-deoxy-4″-(m-hydroxyphenylsulfonylamino)oleandomycin; 11-acetyl-4″-deoxy-4″-(o-hydroxyphenylsulfonylamino)oleandomycin; and 11-propionyl-4″-deoxy-4″-(o-hydroxyphenylsulfonylamino)oleandomycin.

EXAMPLE 19

11-Acetyl-4″-deoxy-4″-(m-carboxamidophenylsulfonylamino)oleandomycin

To 20 ml. of methylene chloride containing 2.91 g. (4.0 mmoles) of 11-acetyl-4″-deoxy-4″-amino-oleandomycin and 434 mg. (4.2 mmoles) of triethylamine is added 898 mg. (4.1 mmoles) of m-carboxamidophenylsulfonyl chloride, and the resulting reaction mixture allowed to stir for 48 hrs. The solvent is removed in vacuo and the residue treated with 25 ml. of acetone. The triethylamine hydrochloride is filtered and the filtrate chromatographed on 160 g. of silica gel. Fractions containing 50 ml. each are collected and examined by thin-layer chromatography to determine the purity of the product. Fractions 66–93 are combined and concentrated under reduced pressure to give 800 mg. of the desired product.

NMR (δ, CDCl$_3$): 2.06 (3H)s; 2.33 (6H)s; 2.70 (2H)s; 3.10 (3H)s; and 7.4–9.0 (4H)m.

EXAMPLE 20

The procedure of Example 19 is repeated, starting with the appropriate 11-alkanoyl-4″-deoxy-4″-amino-oleandomycin and sulfonyl chloride to give the following congeners: 11-propionyl-4″-deoxy-4″-(m-carboxamidophenylsulfonylamino)-oleandomycin; 11-acetyl-4″-deoxy-4″-(o-carboxamidophenylsulfonylamino)oleandomycin; 11-acetyl-4″-deoxy-4″-(p-carboxamidophenylsulfonylamino)oleandomycin; 11-propionyl-4″-deoxy-4″-(o-carboxamidophenylsulfonylamino)oleandomycin; and 11-propionyl-4″-deoxy-4″-(p-carboxamidophenylsulfonylamino)oleandomycin.

EXAMPLE 21

11-Acetyl-4″-deoxy-4″-(p-acetamidophenylsulfonylamino)oleandomycin

A solution of 2.91 g. (4.0 mmoles) of 11-acetyl-4″-deoxy-4″-amino-oleandomycin, 955 mg. (4.1 mmoles) of p-acetamidophenylsulfonyl chloride and 424 mg. (4.2 mmoles) of triethylamine in 20 ml. of methylene chloride is allowed to stir for 48 hrs. at room temperature. The reaction mixture is concentrated under reduced pressure to a foam which is then treated with 10 ml. of acetone. The insoluble triethylamine hydrochloride is filtered and the filtrate chromatographed on 160 g. of silica gel using acetone as the eluate. Cuts 42–86, which by thin-layer chromatography contained most of the pure product, are combined and concentrated in vacuo to give 1.2 g. of the desired product.

NMR (δ, CDCl$_3$): 2.06 (3H)s; 2.23 (3H)s; 2.35 (6H)s; 2.70 (2H)s; 3.13 (3H)s; and 7.6–8.2 (4H)m.

EXAMPLE 22

The procedure of Example 21 is repeated, employing as starting reagents the appropriate 11alkanoyl-4″-deoxy-4″-amino-oleandomycin and requisite sulfonyl chloride, to give the following compounds: 11propionyl-4″-deoxy-4″-(p-acetamidophenylsulfonylamino)oleandomycin; 11-propionyl-4″-deoxy-4″-(o-acetamidophenylsulfonylamino)oleandomycin; 11-acetyl-4″-deoxy-4″-(m-acetamidophenylsulfonylamino)oleandomycin; and 11-propionyl-4″-deoxy-4″-(o-acetamidophenylsulfonylamino)oleandomycin.

EXAMPLE 23

11-Acetyl-4″-deoxy-4″-(p-cyanophenylsulfonylamino)oleandomycin

A solution of 2.55 g. (3.5 mmoles) of 11-acetyl-4″-deoxy-4″-amino-oleandomycin, 734 mg. (3.65 mmoles) and 518 μl. (3.75 mmoles) of triethylamine in 25 ml. of methylene chloride is allowed to stir at room temperature overnight. The solvent is removed in vacuo and the residue treated with 10 ml. of acetone. The insolubles are filtered and the filtrate chromatographed on 120 g. of silica gel using acetone as the eluate and collecting fractions of 10 ml. each. Fractions 47–83 are combined and concentrated under reduced pressure to give 281 mg. of the desired product.

NMR (δ, CDCl$_3$): 2.10 (3H)s; 2.36 (6H)s; 2.71 (2H)d; 3.06 (3H)s; and 7.7–8.4 (4H)m.

EXAMPLE 24

Starting with the requisite 11-alkanoyl-4″-deoxy-4″-amino-oleandomycin and cyanobenzenesulfonyl chloride and employing the procedure of Example 23, the following compounds are synthesized: 11-acetyl-4″-deoxy-4″-(m-cyanophenylsulfonylamino)oleandomycin; 11-propionyl-4″-deoxy-4″-(o-cyanophenylsulfonylamino)-oleandomycin; 11-propionyl-4″-deoxy-4″-(p-cyanophenylsulfonylamino)oleandomycin; 11-acetyl-4″-deoxy-4″-(o-cyanophenylsulfonylamino)oleandomycin; and 11-propionyl-4″-deoxy-4″-(m-cyanophenylsulfonylamino)oleandomycin.

EXAMPLE 25

11-Acetyl-4″-deoxy-4″-(p-trifluoromethylphenylsulfonylamino)oleandomycin

To a solution of 2.55 g. (3.5 mmoles) of 11-acetyl-4″-deoxy-4″-amino-oleandomycin and 518 μl. (3.75 mmoles) of triethylamine in 25 ml. of methylene chloride is added 891 mg. (3.65 mmoles) of p-trifluoromethylphenylsulfonyl chloride, and the resulting reaction mixture allowed to stir for 18 hrs. The solvent is removed under reduced pressure and the residue triturated with 15 ml. of acetone. The solids are filtered and the filtrate chromatographed over silica gel to give 287 mg. of the desired product.

NMR (δ, CDCl$_3$): 2.03 (3H)s; 2.31 (6H)s; 2.63 (2H)d; 3.40 (3H)s; and 7.15–8.3 (4H)m.

EXAMPLE 26

The procedure of Example 25 is repeated, starting with the appropriate reagents, to give the following congeners: 11-propionyl-4″-deoxy-4″-(m-trifluoromethylphenylsulfonylamino)oleandomycin; 11-acetyl-4"-deoxy-4"-(o-trifluoromethylphenylsulfonylamino)oleandomycin; 11-acetyl-4"-deoxy-4"-(m-trifluoromethylphenylsulfonylamino)oleandomycin; 11-propionyl-4"-deoxy-4"-(p-trifluoromethylphenylsulfonylamino)oleandomycin; and 11-propionyl-4"-deoxy-4"'-(o-trifluoromethylphenylsulfonylamino)oleandomycin.

EXAMPLE 27

11-Acetyl-4"-deoxy-4"-(2,2,2-trifluoroethylsulfonylamino)oleandomycin

A solution of 2.55 g (3.5 mmoles) of 11-acetyl-4"-deoxy-4"-amino-oleandomycin, 666 mg. (3.65 mmoles) of 2,2,2-trifluoroethylsulfonyl chloride and 379 mg. (3.75 mmoles) of triethylamine in 25 ml. of methylene chloride is allowed to stir for 30 hrs. at room temperature. An additional 333 mg. of the sulfonyl chloride and 270 μl. of triethylamine are added and the stirring continued for 4 hrs. The solvent is then removed in vacuo and the residue treated with 20 ml. of acetone. The solids are filtered and the filtrate chromatographed on 110 mg. of silica gel using acetone as the eluate and taking 10 ml. fractions. Fractions 50–80 are combined and concentrated to give 385 mg. of the desired product. NMR (δ, CDCl₃): 2.06 (3H)s; 2.26 (6H)s; 2.60 (2H)d; and 3.36 (3H)s.

Similarly, starting with 11-propionyl-4"-deoxy-4"-amino-oleandomycin in place of the 11-acetyl ester and employing the above procedure there is prepared 11-propionyl-4"-deoxy-4"-(2,2,2-trifluoroethylsulfonylamino)oleandomycin.

EXAMPLE 28

11-Acetyl-4"-deoxy-4"-(methylsulfonylamino)oleandomycin

A solution of 2.91 g (4.0 mmoles) of 11-acetyl-4"-deoxy-4"-amino-oleandomycin, 467 mg. (4.1 mmoles) of methylsulfonyl chloride and 424 mg. (4.2 mmoles) of triethylamine in 25 ml. of methylene chloride is allowed to stir at room temperature overnight. The solvent is removed under reduced pressure and the residue treated with 20 ml. of acetone. The triethylamine hydrochloride is filtered and the filtrate containing the product chromatographed on 180 g. of silica gel using acetone as the solvent and taking 6 ml. fractions. Cuts 67–133 are combined and concentrated in vacuo to give 1.2 g. of the desired product.

NMR (δ, CDCl₃): 2.06 (3H)s; 2.28 (6H)s; 3.06 (3H)s; 2.61 (2H)d; and 8.40 (3H)s.

EXAMPLE 29

Starting with the requisite alkyl sulfonyl halide and 11-alkanoyl-4"-deoxy-4"-amino-oleandomycin, and employing the procedure of Example 28, the following compounds are synthesized:

| R₁ | R |
|---|---|
| CH₃CO— | C₂H₅— |
| CH₃CO— | n-C₃H₇— |
| CH₃CO— | i-C₃H₇— |
| CH₃CH₂CO— | CH₃— |
| CH₃CH₂CO— | C₂H₅— |
| CH₃CH₂CO— | n-C₃H₇— |
| CH₃CH₂CO— | i-C₃H₇— |

EXAMPLE 30

11-Acetyl-4"-deoxy-4"-(3,4-dichlorophenylsulfonylamino)oleandomycin

11-Acetyl-4"-deoxy-4"-amino-oleandomycin (2.9 g., 4.0 mmoles), 1.0 g. (4.1 mmoles) of 3,4-dichlorophenylsulfonyl chloride and 0.57 ml. (4.2 mmoles) of triethylamine are combined in 30 ml. of methylene chloride and the resulting solution allowed to stir at room temperature for 18 hrs. The reaction is quenched with 50 ml. of water, and the organic phase washed with a saturated brine solution and dried over sodium sulfate. The solvent is removed in vacuo and the residue chromatographed in 150 g. of silica gel using acetone as the eluate. Those fractions containing the product, as indicated by thin-layer chromatography, are combined and concentrated to dryness to give 1.3 g. of the desired product.

NMR (δ, CDCl₃): 2.0 (3H)s; 2.30 (6H)s; 2.60 (2H)d; 3.06 (3H)s; and 7.2–8.1 (3H)m.

EXAMPLE 31

Following the procedure of Example 30, and starting with the appropriate reagents, the indicated compounds are prepared:

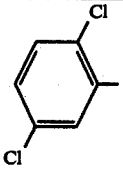

| R | NMR (δ, CDCl₃) |
|---|---|
| 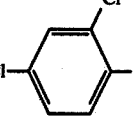 (2,4-dichlorophenyl) | 2.0 (3H)s; 2.36 (6H)s; 2.70 (2H)d; 3.33 (3H)s; and 7.3–8.6 (3H)m. |
| 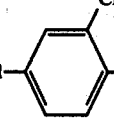 (4-chloro-2-methylphenyl) | 2.10 (3H)s; 2.31 (6H)s; 2.66 (2H)d; 3.30 (3H)s; and 7.2–8.4 (3H)m. |
| 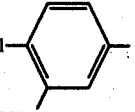 (2-methyl-5-chlorophenyl) | 2.03 (3H)s; 2.30 (6H)s; 2.66 (3H)s; 3.10 (3H)s; and 7.1–8.1 (3H)m*. |
| 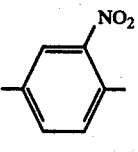 (2-nitro-4-chlorophenyl) | 2.06 (3H)s; 2.33 (6H)s; 2.70 (2H)d; 3.13 (3H)s; and 7.4–8.6 (3H)m. |
| 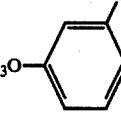 (4-nitro-2-chlorophenyl) | 2.06 (3H)s; 2.40 (6H)s; 2.66 (2H)d; 3.25 (3H)s; and 7.2–8.6 (3H)m*. |
| 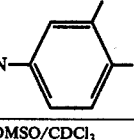 (3-methoxy-4-nitrophenyl) | 2.06 (3H)s; 2.33 (6H)s; 2.63 (2H)d; 2.81 (3H)s; 3.63 (3H)s; and 7.0–8.2 (3H)m*. |
| (2,4-dinitrophenyl) | 2.06 (3H)s; 2.36 (6H)s; and 8.4–9.0 (3H)m*. |

*NMR: DMSO/CDCl₃

EXAMPLE 32

The procedure of Example 30 is again repeated, starting with the requisite 11-alkanoyl-4″-deoxy-4″-amino-oleandomycin and sulfonyl chloride, to give the following analogs: 11-acetyl-4″-deoxy-4″-(2,6-dichlorophenylsulfonylamino)oleandomycin; 11-propionyl-4″-deoxy-4″-(4-methyl-2-chlorophenylsulfonylamino)oleandomycin; 11-propionyl-4″-deoxy-4″-(2-methyl-5-chlorophenylsulfonylamino)oleandomycin; 11-propionyl-4″-deoxy-4″-(2-nitro-4-chlorophenylsulfonylamino)oleandomycin; 11-acetyl-4″-deoxy-4″-(3-nitro-4-chlorophenylsulfonylamino)oleandomycin; 11-acetyl-4″-deoxy-4″-(3-nitro-5-chlorophenylsulfonylamino)oleandomycin; 11-propionyl-4″-deoxy-4″-(3-methoxy-5-nitrophenylsulfonylamino)-oleandomycin; 11-acetyl-4″-deoxy-4″-(3-nitro-4-methylphenylsulfonylamino)oleandomycin; 11-acetyl-4″-deoxy-4″-(3,5-dinitrophenylsulfonylamino)oleandomycin; 11-acetyl-4″-deoxy-4″-(2,6-dimethoxyphenylsulfonylamino)oleandomycin; 11-propionyl-4″-deoxy-4″-(2,4-dimethoxyphenylsulfonylamino)oleandomycin; 11-acetyl-4″-deoxy-4″-(2-methyl-5-methoxyphenylsulfonylamino)oleandomycin; 11-acetyl-4″-deoxy-4″-(2,3-dimethylphenylsulfonylamino)oleandomycin; 11-propionyl-4″-deoxy-4″-(2,4-dimethylphenylsulfonylamino)oleandomycin; and 11-acetyl-4″-deoxy-4″-(3-nitro-4-methylsulfonylamino)oleandomycin.

EXAMPLE 33

11-Acetyl-4″-deoxy-4″-(2,3,4-trichlorophenylsulfonylamino)oleandomycin

A solution of 2.9 g. (4.0 mmoles) of 11-acetyl-4″-amino-oleandomycin, 1.15 g. (4.1 mmoles) of 2,3,4-trichlorophenylsulfonyl chloride and 0.57 ml. (4.2 mmoles) of triethylamine in 30 ml. of methylene chloride is allowed to stir at room temperature for 18 hrs. The organic layer is washed with water (1 × 50 ml.) and a saturated brine solution (1 × 50 ml.) and subsequently dried over sodium sulfate. The solvent is removed in vacuo and the residue is removed in vacuo and the residue chromatographed on 150 g. of silica gel using acetone as the solvent, taking fraction of 7 ml. each. Fractions 60–100 are combined and concentrated to give 800 mg. of the desired product.

NMR (δ, CDCl₃): 2.06 (3H)s; 2.33 (6H)s; 2.63 (2H)d; 3.2 (3H)s; and 7.2–8.2 (2H)m.

Similarly, by starting with the appropriate reagents and following the above procedure, the following compounds are synthesized: 11-acetyl-4″-deoxy-4″-(3,4,5-trichlorophenylsulfonylamino)oleandomycin; 11-propionyl-4″-deoxy-4″-(2,4,6-trichlorophenylsulfonylamino)oleandomycin; and 11-acetyl-4″-deoxy-4″-(2,3,5-trichlorophenylsulfonylamino)oleandomcyin.

EXAMPLE 34

11-Acetyl-4″-deoxy-4″-(2-hydroxy-3,5-dichlorophenylsulfonylamino)oleandomycin

The procedure of Example 33 is repeated, starting with 2.55 g. (3.5 mmoles), 954 mg. (3.65 mmoles) of 2-hydroxy-3,5-dichlorophenylsulfonyl chloride and 518 μl. (3.75 mmoles) of triethylamine in 25 ml. of methylene chloride to give, after chromatographing on 220 g. of silica gel, 483 mg. of the desired product.

NMR (δ, CDCl₃/DMSO): 2.03 (3H)s; 2.50 (6H)s; 3.05 (3H)s; and 7.2–7.8 (2H)m.

EXAMPLE 35

Starting with the requisite 11-alkanoyl-4″-deoxy-4″-amino-oleandomycin and sulfonyl chloride and employing the procedure of Example 33, the following congeners are prepared:

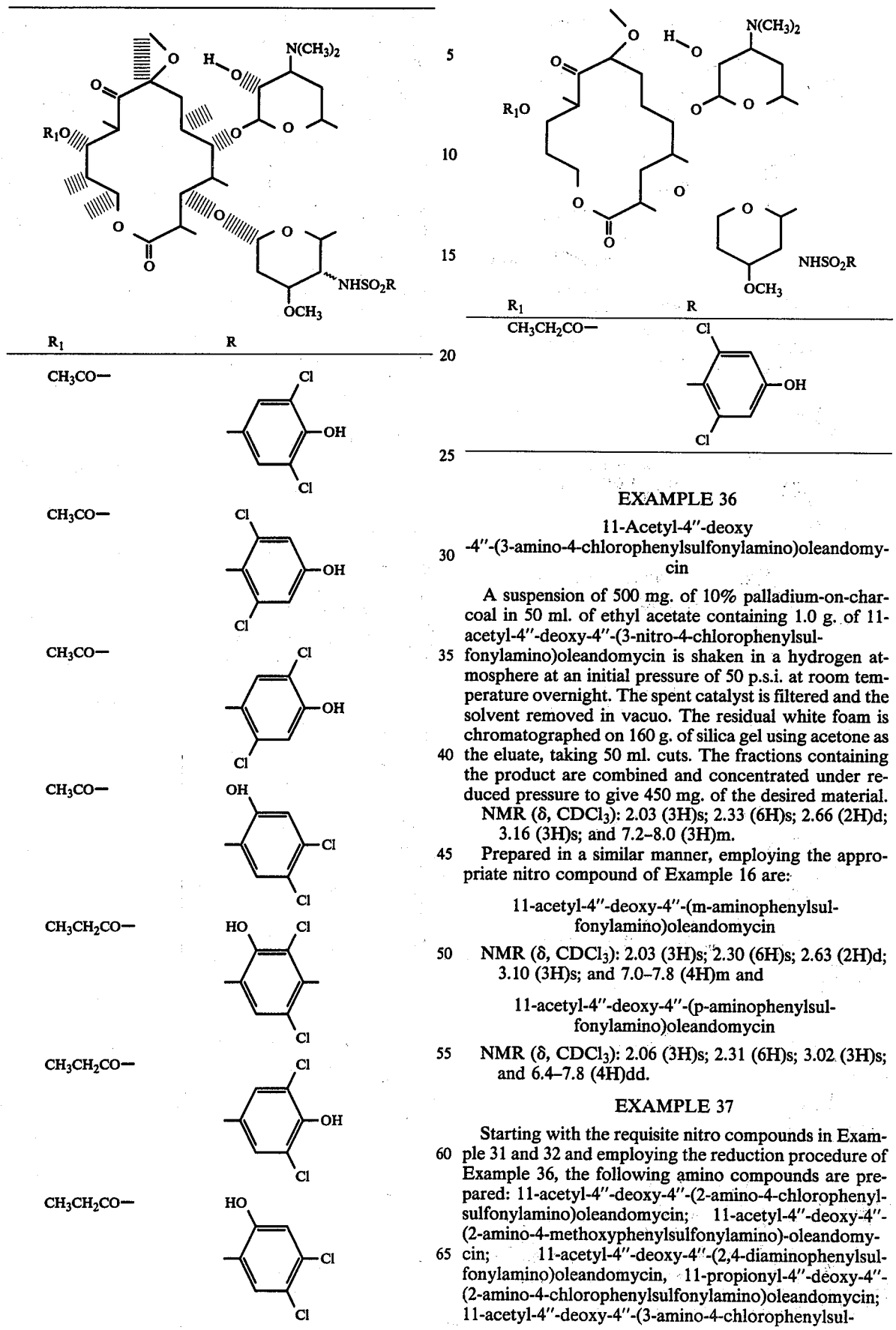

EXAMPLE 36

11-Acetyl-4"-deoxy-4"-(3-amino-4-chlorophenylsulfonylamino)oleandomycin

A suspension of 500 mg. of 10% palladium-on-charcoal in 50 ml. of ethyl acetate containing 1.0 g. of 11-acetyl-4"-deoxy-4"-(3-nitro-4-chlorophenylsulfonylamino)oleandomycin is shaken in a hydrogen atmosphere at an initial pressure of 50 p.s.i. at room temperature overnight. The spent catalyst is filtered and the solvent removed in vacuo. The residual white foam is chromatographed on 160 g. of silica gel using acetone as the eluate, taking 50 ml. cuts. The fractions containing the product are combined and concentrated under reduced pressure to give 450 mg. of the desired material.

NMR ($\delta$, CDCl$_3$): 2.03 (3H)s; 2.33 (6H)s; 2.66 (2H)d; 3.16 (3H)s; and 7.2–8.0 (3H)m.

Prepared in a similar manner, employing the appropriate nitro compound of Example 16 are:

11-acetyl-4"-deoxy-4"-(m-aminophenylsulfonylamino)oleandomycin

NMR ($\delta$, CDCl$_3$): 2.03 (3H)s; 2.30 (6H)s; 2.63 (2H)d; 3.10 (3H)s; and 7.0–7.8 (4H)m and 11-acetyl-4"-deoxy-4"-(p-aminophenylsulfonylamino)oleandomycin NMR ($\delta$, CDCl$_3$): 2.06 (3H)s; 2.31 (6H)s; 3.02 (3H)s; and 6.4–7.8 (4H)dd.

EXAMPLE 37

Starting with the requisite nitro compounds in Example 31 and 32 and employing the reduction procedure of Example 36, the following amino compounds are prepared: 11-acetyl-4"-deoxy-4"-(2-amino-4-chlorophenylsulfonylamino)oleandomycin; 11-acetyl-4"-deoxy-4"-(2-amino-4-methoxyphenylsulfonylamino)-oleandomycin; 11-acetyl-4"-deoxy-4"-(2,4-diaminophenylsulfonylamino)oleandomycin, 11-propionyl-4"-deoxy-4"-(2-amino-4-chlorophenylsulfonylamino)oleandomycin; 11-acetyl-4"-deoxy-4"-(3-amino-4-chlorophenylsulfonylamino)oleandomycin; 11-acetyl-4"-deoxy-4"-(3-amino-5-chlorophenylsulfonylamino)oleandomycin; 11-propionyl-4"-deoxy-4"-(3-methoxy-5-aminophenylsulfonylamino)oleandomycin; 11-acetyl-4"-deoxy-4"-(3-amino-4-methylphenylsulfonylamino)oleandomycin; and 11-acetyl-4"-deoxy-4"-(3,5-diaminophenylsulfonylamino)oleandomycin.

EXAMPLE 38

11-Acetyl-4"-deoxy-4"-(3-methyl-2-thienylsulfonylamino)oleandomycin

To 100 g. (0.13 mole) of 11-acetyl-4"-deoxy-4"-amino-oleandomycin in 900 ml. of methylene chloride is added 593 ml. of triethylamine, and the solution allowed to stir for 10 minutes. 3-Methyl-2-thienylsulfonyl chloride (41.9 g.; 0.213 mole) in 300 ml. of methylene chloride is subsequently added dropwise over a period of one hour and the reaction mixture allowed to stir at room temperature for 48 hours. The reaction mixture is added to 2 l. of water and the organic layer separated, washed successively with water (2 × 250 ml.) and a brine solution (1 × 250 ml.) and dried over sodium sulfate. The solvent is removed in vacuo and the residue chromatographed on a 105 cm. × 6.5 cm. column containing 1.5 kg. of silica gel. The product, which is eluted with acetone, is collected in the 2.3 l. to 6 l. eluate fractions. The fractions are combined, and the solvent removed under reduced pressure to give a foam. Treatment of the residual foam with diethyl ether gave 66.4 g. of the desired product, m.p. 184°–185.5° C.

NMR (δ, CDCl$_3$): 2.04 (3H)s; 2.41 (6H)s; 2.46 (3H)s; 2.62 (2H)m; 3.02 (3H)s; 6.84 and 7.32 (2H).

To 2 g. of the above free base in 15 ml. of ethyl acetate is added 0.12 ml. of phosphoric acid and the resulting solution allowed to stir at room temperature. After 20 minutes crystals commence to form and after 2 hours are filtered, washed with ethyl acetate and dried to give 1.3 g. of 11-acetyl-4"-deoxy-4"-(3-methyl-2-thienylsulfonylamino)oleandomycin phosphate.

NMR (δ, CD$_3$OD): 2.01 (3H)s; 2.45 (3H)s; 2.56 (2H)m; 2.83 (6H)s; 3.0 (3H)s; 6.88 and 7.42 (2H).

EXAMPLE 39

The procedure of Example 38 is repeated, starting with the appropriate sulfonyl chloride and 11-acetyl-4"-deoxy-4"-amino-oleandomycin to give the following congeners:

| R$_1$ | NMR (δ, CDCl$_3$) |
|---|---|
| CH$_3$—furan—CH$_3$ (2,5-dimethylfuran) | 2.08 (3H)s; 2.33 (6H)s; 2.38 (3H)s; 2.68 (2H)m; 3.27 (3H)s; 6.08 and 6.92 (2H). |
| N-methyl-2,5-dimethylpyrrole (CH$_3$—pyrrole N-CH$_3$) | 2.08 (3H)s; 2.36 (6H)s; 2.68 (2H)m; 3.30 (3H)s; 3.71 (3H); 6.44–6.70 (1H)m and 7.18–7.39 (2H)m. |
| CH$_3$—thiophene—CH$_3$ | 2.03 (3H)s; 2.25 (3H)s; 2.51 (6H)s; 2.61 (2H)m; 3.15 (3H)s; 7.07 (1H)m and 7.38 (1H)m. |
| C$_2$H$_5$—thiophene | 2.06 (3H)s; 2.33 (6H)s; 2.65 (2H)m; 3.22 (3H)s; 6.73 and 7.45 (2H). |
| CH$_3$—thiophene | 2.08 (3H)s; 2.34 (6H)s; 2.54 (3H)s; 2.67 (2H)s; 3.25 (3H)s; 6.73 and 7.46 (2H). |

EXAMPLE 40

The procedure of Example 38 is again repeated, starting with the requisite sulfonyl chloride and appropriate 11-alkanoyl-4"-deoxy-4"-aminooleandomycin, to give the following analogs: 11-acetyl-4"-deoxy-4"-(3-ethyl-2-thienylsulfonylamino)oleandomycin; 11-propionyl-4"-deoxy-4"-(3-methyl-2-thienylsulfonylamino)oleandomycin; 11-acetyl-4"-deoxy-4"-(5-ethyl-2-pyrrylsulfonylamino)oleandomycin; 11-propionyl-4"-deoxy-4"-(4-ethyl-2-thienylsulfonylamino)oleandomycin; 11-acetyl-4"-deoxy-4"-(1-ethyl-3-pyrrylsulfonylamino)-oleandomycin; 11-propionyl-4"-deoxy-4"-(5-ethyl-2-furylsulfonylamino)oleandomycin; 11-acetyl-4"-deoxy-4"-(4-ethyl-3-furylsulfonylamino)oleandomycin; and 11-acetyl-4"-deoxy-4"-(3-ethyl-2-furylsulfonylamino)oleandomycin.

EXAMPLE 41

11-Acetyl-4"-deoxy-4"-(5-carbomethoxy-2-pyrrylsulfonylamino)oleandomycin

A solution of 2.96 g. (.0041 mole) of 11-acetyl-4"-deoxy-4"-amino-oleandomycin and 0.62 ml. of triethylamine in 50 ml. of dry methylene chloride cooled to ice bath temperatures is treated portionwise with 1.0 g. (.0044 mole) of 2-carbomethoxy-5-pyrrylsulfonyl chloride. The reaction mixture is allowed to warm to room temperature and stir for 3.5 hours, and is then poured into 200 ml. of water. The pH of the aqueous layer is adjusted to 9.5 with 1N aqueous sodium hydroxide and the methylene chloride layer separated, washed successively with water and saturated brine and dried over sodium sulfate. Removal of the solvent under reduced pressure gives 3.8 g. of the crude product as a white foam.

The above foam is subsequently chromatographed on a silica gel column 3.25 cm. × 38 cm. using acetone as the eluate. Fractions 40–220, comprised of approximately 10–12 ml. each, are collected and combined. Removal of the eluate solvent in vacuo gives 3.4 g. of the desired product as a white foam.

NMR (δ, CDCl$_3$): 2.05 (3H)s; 2.58 (6H)s; 2.67 (2H)m; 3.25 (3H)s; 3.90 (3H)s; 7.20 (1H)m and 7.52 (1H)m.

EXAMPLE 42

The procedure of Example 41 is repeated, starting with the appropriate sulfonyl chloride and 11-acetyl-4"-deoxy-4"-amino-oleandomycin, to give the following analogs:

amino-oleandomycin, to give the following compounds:

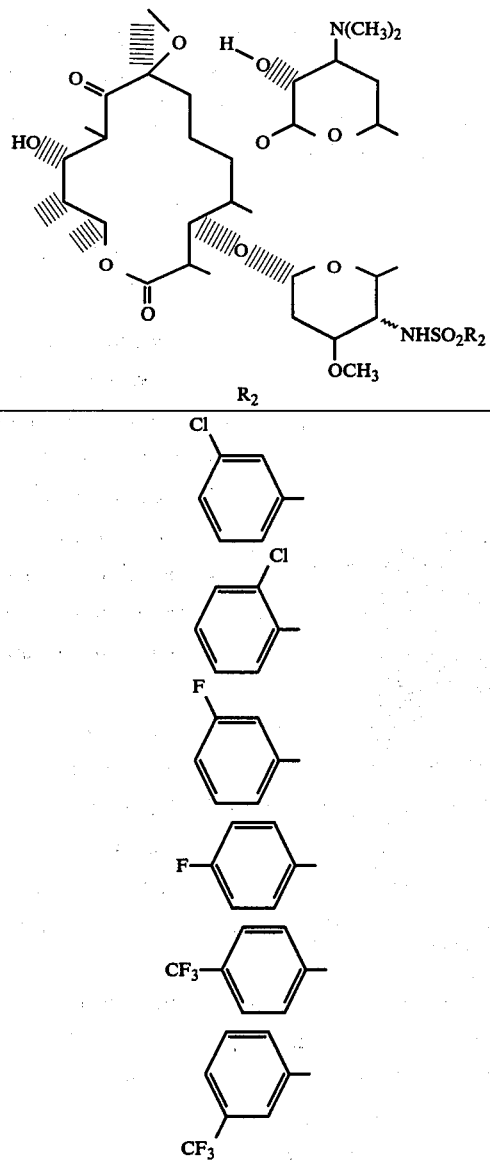

| R$_1$ | NMR (δ,CDCl$_3$) |
|---|---|
| CH$_3$O$_2$C—[S] | 2.09 (3H)s; 2.32 (6H)s; 2.69 (2H)m; 3.22 (3H)s; 3.95(3H)s; 7.61 and 7.75 (2H). |
| CH$_3$O$_2$C—[S] | 2.11 (3H)s; 2.34 (6H)s; 2.70 (2H)m; 3.24 (3H)s; 3.94 (3H)s; 8.06 and 8.28 (2H). |
| CH$_3$O$_2$C—[O] | 2.08 (3H)s; 2.29 (6H)s; 2.67 (2H)s; 3.18 (3H)s; 3.94 (3H)s; 7.02 and 7.20 (2H). |

EXAMPLE 43

4"-Deoxy-4"-(p-chlorophenylsulfonylamino)oleandomycin

A solution of 3.0 g. of 4"-deoxy-4"-amino-oleandomycin, 865 mg. of p-chlorophenylsulfonyl chloride and 424 mg. of triethylamine in 25 ml. of methylene chloride is allowed to stir at room temperature overnight. The solvent is removed in vacuo and the residue treated with 20 ml. of acetone. The insoluble triethylamine hydrochloride is filtered and the filtrate chromatographed on 180 g. of silica gel using acetone as the eluting solvent and taking 50 ml. cuts. Fractions 18–27 are combined and concentrated under reduced pressure to give 1.10 g. of the desired product.

NMR (δ, CDCl$_3$): 2.33 (6H); 2.83 (2H)d; 3.06 (3H); and 7.2–8.4 (4H)m.

EXAMPLE 44

The procedure of Example 43 is repeated, starting with the appropriate sulfonyl chloride and 4"-deoxy-4"-

EXAMPLE 45

4"-Deoxy-4"-(p-toluenesulfonylamino)oleandomycin

By a procedure similar to Example 43, 30 g. (4.0 mmoles) of 4"-deoxy-4"-amino-oleandomycin, 782 mg. (4.1 mmoles) of p-toluenesulfonyl chloride and 424 mg. (4.2 mmoles) of triethylamine in 25 ml. of methylene chloride are allowed to stir at ambient temperatures overnight. On work-up the crude product is chromatographed on 180 g. of silica gel, taking 10 ml. cuts. Fractions 90–148 are combined and concentrated to dryness to give 1.4 g. of the desired product.

NMR (δ, CDCl$_3$): 2.33 (6H)s; 2.46 (3H)s; 2.83 (2H)d; 3.10 (3H)s; and 7.10–8.0 (4H)m.

Also, by a similar procedure, is prepared 4"-deoxy-4"-(2-thienylsulfonylamino)oleandomycin.

NMR (δ, CDCl$_3$): 2.29 (6H)s; 2.88 (2H)m; 3.2 (3H)s; 5.6 (1H)m and 7.33 (3H)m.

EXAMPLE 46

Starting with 4''-deoxy-4''-amino-oleandomycin and the requisite sulfonyl chloride and employing the procedure of Example 43, the following congeners are synthesized:

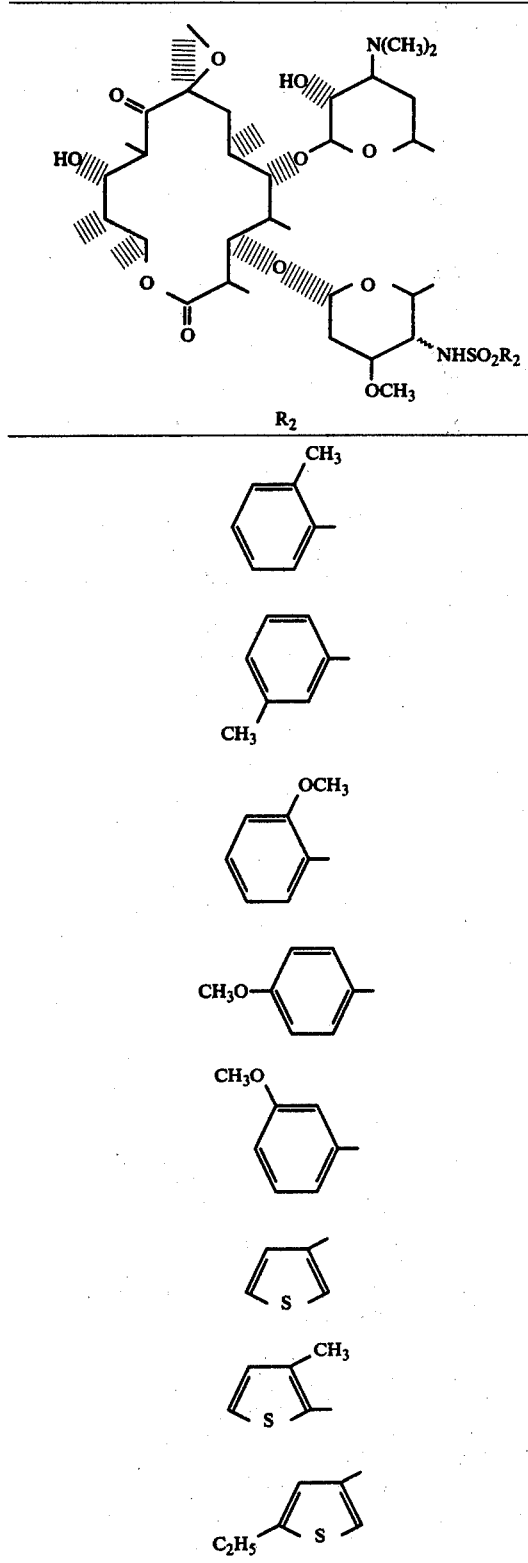

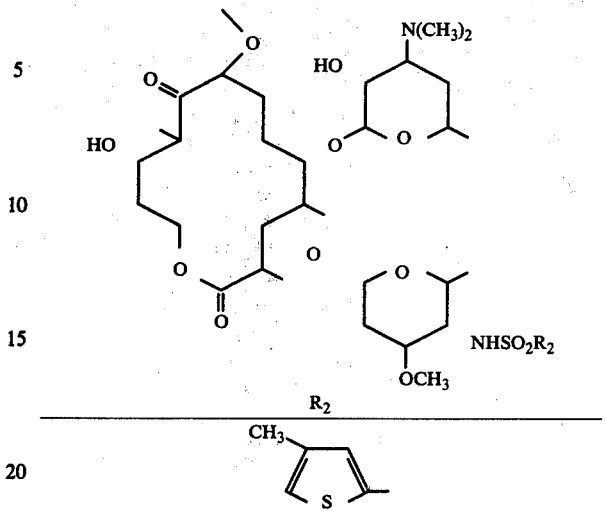

EXAMPLE 47

11-Acetyl-4''-deoxy-4''-(vinylsulfonylamino)oleandomycin

To a solution of 17.1 g. (82.3 mmoles) of $\beta$-bromoethanesulfonyl chloride in 200 ml. of methylene chloride cooled to $-78°$ C. and maintained under a nitrogen atmosphere is added a cold ($-78°$ C.) solution of 30 g. (41.1 mmoles) of 11-acetyl-4''-deoxy-4''-amino-oleandomycin and 16.7 g. (164 mmoles) of triethylamine in 100 ml. of methylene chloride. After stirring at $-78°$ C. for 1.3 hrs. the reaction mixture is poured into water and the pH adjusted to 7.3 by the addition of solid sodium bicarbonate. The organic phase is separated, dried over sodium sulfate and concentrated in vacuo to give 43.5 g. of a yellow foam. The residual material is slurried in ether and filtered. The filtrate is concentrated under reduced pressure to give 20.3 g. of the crude product which is chromatographed on 800 g. of silica gel using chloroform-methanol (95:5; v:v) as the eluting solvent. The fractions containing the product are combined and concentrated to give 5.1 g.

NMR ($\delta$, CDCl$_3$): 2.10 (3H)s; 2.37 (6H)s; 2.70 (2H)d; 3.43 (3H)s; and 5.7–7.06 (3H)m.

EXAMPLE 48

11-Acetyl-4''-deoxy-4''-($\beta$-bromoethylsulfonylamino)oleandomycin

To a solution of 500 mg. (0.68 mmoles) of 11-acetyl-4''-deoxy-4''-aminooleandomycin and 882 mg. (8.2 mmoles) of 2,6-lutidine in 4 ml. of methylene chloride precooled to $-4°$ C. and under a nitrogen atmosphere is added 854 mg. (4.0 mmoles) of $\beta$-bromoethane sulfonyl chloride in 2 ml. of methylene chloride cooled to $-2°$ C. After stirring at $-2°$ C. for 1.75 hrs., the reaction mixture is poured into a mixture of water and methylene chloride and the pH adjusted to 7.0 with solid sodium bicarbonate. The organic phase is separated, dried over sodium sulfate and concentrated to am amber oil. The residual oil is chromatographed on 42 g. of silica gel, using chloroform-methanol (95:5; v:v) as the eluate solvent, to give 52.5 mg. of the desired product.

NMR ($\delta$, CDCl$_3$): 2.08 (3H)s; 2.33 (6H)s; 2.65 (2H)s; and 3.46 (3H)s.

EXAMPLE 49

11-Acetyl-4''-deoxy-4''-(2-diethylaminoethylsulfonylamino)oleandomycin

To a solution of 1.0 g. (1.22 mmoles) of 11-acetyl-4''-deoxy-4''-(vinylsulfonylamino)oleandomycin in 5 ml. of benzene is added 892 mg. (12.2 mmoles) of diethylamine, and the resulting reaction mixture allowed to stir under a nitrogen atmosphere at ambient temperature for 48 hrs. The solvent and excess diethylamine is removed in vacuo and the product obtained as a white foam which slowly crystallizes, 940 mg., m.p. 85°–99° C. NMR (δ, CDCl$_3$): 2.05 (3H)s; 2.30 (6H)s; 2.36–2.73 (4H)q; 2.63 (2H)s; and 3.4 (3H)s.

EXAMPLE 50

The procedure of Example 49 is repeated, starting with the appropriate 11-alkanoyl-4''-deoxy-4''-amino-oleandomycin and secondary amino to give the following compounds:

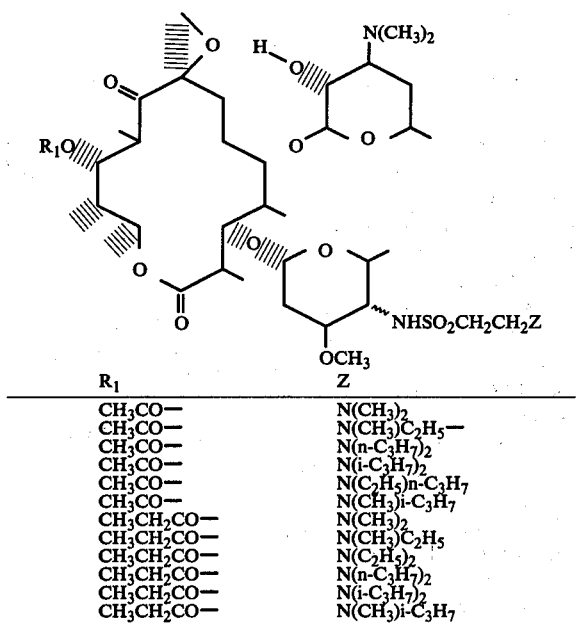

| R$_1$ | Z |
|---|---|
| CH$_3$CO— | N(CH$_3$)$_2$ |
| CH$_3$CO— | N(CH$_3$)C$_2$H$_5$— |
| CH$_3$CO— | N(n-C$_3$H$_7$)$_2$ |
| CH$_3$CO— | N(i-C$_3$H$_7$)$_2$ |
| CH$_3$CO— | N(C$_2$H$_5$)n-C$_3$H$_7$ |
| CH$_3$CO— | N(CH$_3$)i-C$_3$H$_7$ |
| CH$_3$CH$_2$CO— | N(CH$_3$)$_2$ |
| CH$_3$CH$_2$CO— | N(CH$_3$)C$_2$H$_5$ |
| CH$_3$CH$_2$CO— | N(C$_2$H$_5$)$_2$ |
| CH$_3$CH$_2$CO— | N(n-C$_3$H$_7$)$_2$ |
| CH$_3$CH$_2$CO— | N(i-C$_3$H$_7$)$_2$ |
| CH$_3$CH$_2$CO— | N(CH$_3$)i-C$_3$H$_7$ |

EXAMPLE 51

11-Acetyl-4''-deoxy-4''-(methylthioethylsulfonylamino)oleandomycin

A suspension of 800 mg. (0.98 mmole) of 11-acetyl-4''-deoxy-4''-(vinylsulfonylamino)oleandomycin and 475 mg. (3 mmoles) of potassium carbonate in 10 ml. of benzene is stirred while methyl mercaptan is bubbled into the suspension for 30 sec. The tightly stoppered container is allowed to stir overnight at room temperature. The excess mercaptan is removed under reduced pressure, and the reaction mixture added to a mixture of benzene-water. The organic layer is separated, dried over sodium sulfate and concentrated in vacuo to give 805 mg. of the product as an oil.

NMR (δ, CDCl$_3$): 1.98 (3H)s; 2.05 (3H)s; 2.20 (6H)s; 2.57 (2H)s; and 3.30 (3H)s.

EXAMPLE 52

Starting with the appropriate mercaptan and 11-acetyl-4''-deoxy-4''-(vinylsulfonylamino)oleandomycin and employing the procedure of Example 51, the following compounds are synthesized:

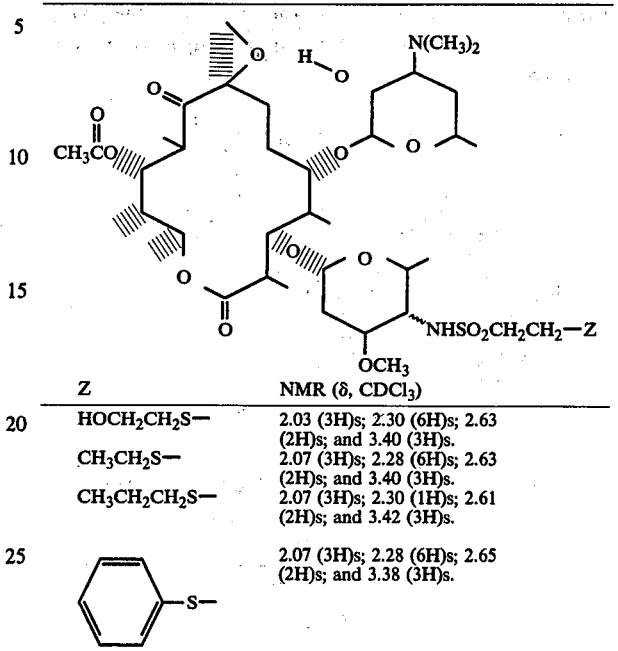

| Z | NMR (δ, CDCl$_3$) |
|---|---|
| HOCH$_2$CH$_2$S— | 2.03 (3H)s; 2.30 (6H)s; 2.63 (2H)s; and 3.40 (3H)s. |
| CH$_3$CH$_2$S— | 2.07 (3H)s; 2.28 (6H)s; 2.63 (2H)s; and 3.40 (3H)s. |
| CH$_3$CH$_2$CH$_2$S— | 2.07 (3H)s; 2.30 (1H)s; 2.61 (2H)s; and 3.42 (3H)s. |
| C$_6$H$_5$—S— | 2.07 (3H)s; 2.28 (6H)s; 2.65 (2H)s; and 3.38 (3H)s. |

EXAMPLE 53

The procedure of Example 51 is again repeated, starting with the appropriate 11-alkanoyl-4''-deoxy-4''-(vinylsulfonylamino)oleandomycin and mercaptan to give the following analogs:

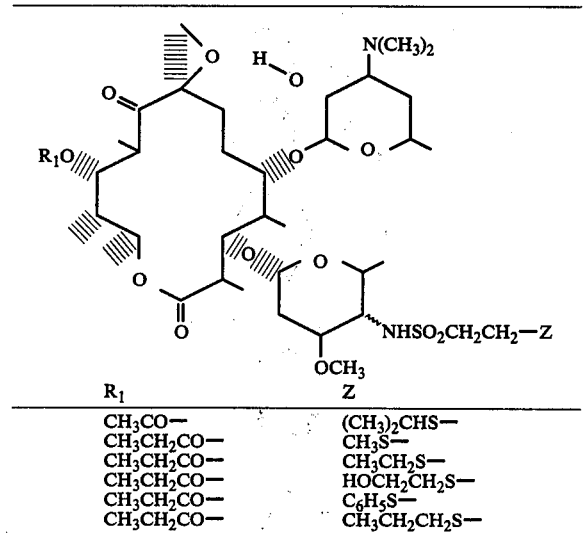

| R$_1$ | Z |
|---|---|
| CH$_3$CO— | (CH$_3$)$_2$CHS— |
| CH$_3$CH$_2$CO— | CH$_3$S— |
| CH$_3$CH$_2$CO— | CH$_3$CH$_2$S— |
| CH$_3$CH$_2$CO— | HOCH$_2$CH$_2$S— |
| CH$_3$CH$_2$CO— | C$_6$H$_5$S— |
| CH$_3$CH$_2$CO— | CH$_3$CH$_2$CH$_2$S— |

EXAMPLE 54

11-Acetyl-4''-deoxy-4''-(morpholinoethylsulfonylamino)oleandomycin

To a solution of 2.0 g. (2.44 mmoles) of 11-acetyl-4''-deoxy-4''-(vinylsulfonylamino)oleandomycin in 50 ml. of benzene is added 2.1 g. (24.4 mmoles) of morpholine, and the resulting reaction mixture allowed to stir under a nitrogen atmosphere for 40 hrs. at room temperature.

The solvent and excess morpholine are removed in vacuo to give the crude product as a foam. The residue is triturated in hexane for one hour followed by recrystallization from ethylacetate-hexane, 890 mg., m.p. 95° C.

NMR (δ, CDCl$_3$): 2.06 (3H)s; 2.30 (6H)s; and 3.42 (3H)s.

EXAMPLE 55

11-Acetyl-4″-deoxy-4″-(2-thienylsulfonylamino)oleandomycin hydrochloride

To 8.7 g. of 11-acetyl-4″-deoxy-4″-(2-thienylsulfonylamino)oleandomycin in 50 ml. of dry ethylacetate is added 10 ml. of a 1N ethylacetate solution of hydrogen chloride is added. The solution is concentrated to dryness in vacuo and the residual mono-hydrochloride salt is triturated with ether and filtered.

EXAMPLE 56

11-Acetyl-4″-deoxy-4″-(2-thienylsulfonylamino)oleandomycin phosphate

To a solution of 15.0 g. of 11-acetyl-4″-deoxy-4″-(2-thienylsulfonylamino)oleandomycin in 100 ml. of ethyl acetate is added 1.0 ml. of phosphoric acid. The resulting suspension is allowed to stir for four hours at room temperature. The solids are filtered, washed with ethyl acetate and dried to give 12.5 g. of the desired salt, m.p. 168° C. (dec.).

In a similar manner is prepared 11-acetyl-4″-deoxy-4″-(3-methyl-2-thienylsulfonylamino)oleandomycin phosphate, m.p. 184°-188° C. and 11-acetyl-4″-deoxy-4″-(p-chlorophenylsulfonylamino)oleandomycin phosphate, m.p. 204°-205° C.

PREPARATION A

4″-Deoxy-4″-oxo-oleandomycins

I. 11-Acetyl-4″-deoxy-4″-oxo-oleandomycin a. 11,2′-Diacetyl-4″-deoxy-4″-oxo-oleandomycin To a 4.5 g. of N-chlorosuccinimide, 50 ml. of benzene and 150 ml. of toluene in a dry flask fitted with a magnetic stirrer and nitrogen inlet and cooled to −5° C. is added 3.36 ml. of dimethylsulfide. After stirring at 0° C. for 20 min., the contents are cooled to −25° C. and treated with 5.0 g. of 11,2′-diacetyl-oleandomycin in 100 ml. of toluene. Cooling and stirring are continued for 2 hrs. followed by the addition of 4.73 ml. of triethylamine. The reaction mixture is allowed to stir at 0° C. for 15 min., and is subsequently poured into 500 ml. of water. The pH is adjusted to 9.5 with 1N aqueous sodium hydroxide and the organic layer separated, washed with water and a brine solution and dried over sodium sulfate. Removal of the solvent in vacuo gives 4.9 g. of the desired product as a foam.

NMR (δ, CDCl$_3$): 3.48 (3H)s, 2.61 (2H)m, 2.23 (6H)s and 2.03 (6H)s.

b. 11-Acetyl-4″-deoxy-4″-oxo-oleandomycin

A solution of 4.0 g. of 11,2′-diacetyl-4″-deoxy-4″-oxo-oleandomycin in 75 ml. of methanol is allowed to stir at room temperature overnight. The reaction mixture is concentrated under reduced pressure to give the product as a foam. A diethyl ether solution of the residue, on treatment with hexane, gives 2.6 g. of the product as a white solid, m.p. 112°-117° C.

NMR (δ, CDCl$_3$): 3.43 (3H)s, 2.60 (2H)m, 2.23 (6H)s and 2.01 (3H)s.

Similarly, by employing 11,2′-dipropionyl-4″-deoxy-4″-oxo-oleandomycin or 11-propionyl-2′-acetyl-4″-deoxy-4″-oxo-oleandomycin in the above procedure, 11-propionyl-4″-deoxy-4″-oxo-oleandomycin is prepared.

II. 4″-Deoxy-4″-oxo-oleandomycin a. 2′-Acetyl-4″-deoxy-4″-oxo-oleandomycin

Dimethylsulfide (0.337 ml.) is added to a turbid solution of 467 mg. of N-chlorosuccinimide in 20 ml. of toluene and 6 ml. of benzene cooled to −5° C. and maintained under a nitrogen atmosphere. After stirring at 0° C. for 20 min. the mixture is cooled to −25° C. and 1.46 g. of 2′-acetyloleandomycin and 15 ml. of toluene are added. Stirring is continued for 2 hrs. at −20° C. followed by the addition of 0.46 ml. of triethylamine. The reaction mixture is maintained at −20° C. for an additional 5 min. and then allowed to warm to 0° C. The mixture is poured, with stirring, into 50 ml. of water and 50 ml. of ethyl acetate. The pH of the aqueous mixture is adjusted to 9.5 by the addition of aqueous sodium hydroxide solution. The organic layer is subsequently separated, dried over sodium sulfate and concentrated in vacuo to a white foam (1.5 g.). Trituration with diethyl ether gives 864 mg. of crude product, which on recrystallization twice from methylene chloride-diethyl ether gives 212 mg. of the pure product, m.p. 183°-185.5° C.

Anal. Calc'd for $C_{37}H_{61}O_{13}N$: C, 61.1; H, 8.5; N, 1.9. Found: C, 60.9; H, 8.4; N, 1.9.

NMR (δ, CDCl$_3$): 5.60 (1H)m, 3.50 (3H)s, 2.73 (2H)m, 2.23 (6H)s and 2.03 (3H)s.

b. 4″-Deoxy-4″-oxo-oleandomycin

A solution of 1.0 g. of 2′-acetyl-4″-deoxy-4″-oxo-oleandomycin in 20 ml. of methanol is allowed to stir at room temperature overnight. The solution is concentrated in vacuo to give the desired product as a white foam, 937 mg.

NMR (δ, CDCl$_3$): 5.60 (1H)m, 3.50 (3H)s, 2.85 (2H)m and 2.26 (6H)s.

PREPARATION B

4″-Deoxy-4″-amino-oleandomycins

I. 11-Acetyl-4″-deoxy-4″-amino-oleandomycin

To a suspension of 10 g. of 10% palladium-on-charcoal in 100 ml. of methanol is added 21.2 g. of ammonium acetate and the resulting slurry is treated with a solution of 20 g. of 11-acetyl-4″-deoxy-4″-oxo-oleandomycin in 100 ml. of the same solvent. The suspension is shaken at room temperature in a hydrogen atmosphere at an initial pressure of 50 p.s.i. After 1.5 hrs., the catalyst is filtered and the filtrate is added with stirring to a mixture of 1200 ml. of water and 500 ml. of chloroform. The pH is adjusted from 6.4 to 4.5 and the organic layer is separated. The aqueous layer, after a further extraction with 500 ml. of chloroform, is treated with 500 ml. of ethyl acetate and the pH adjusted to 9.5 with 1N sodium hydroxide. The ethyl acetate layer is separated and the aqueous layer extracted again with ethyl acetate. The ethyl acetate extracts are combined, dried over sodium sulfate and concentrated to a yellow foam (18.6 g.), which on crystallization from diisopropyl ether, provides 6.85 g. of the purified product, m.p. 157.5°-160° C.

NMR (δ, CDCl$_3$): 3.41 (3H)s, 2.70 (2H)m, 2.36 (6H)s and 2.10 (3H)s.

The other epimer, which exists in the crude foam to the extent of 20–25%, is obtained by gradual concentration and filtration of the mother liquors.

In a similar manner, starting with 11-propionyl-4"-deoxy-4"-oxo-oleandomycin in the above procedure, gives 11-propionyl-4"-deoxy-4"-amino-oleandomycin.

II. 4"-Deoxy-4"-amino-oleandomycin

A solution of 20 g. of 2'-acetyl-4"-deoxy-4"-oxo-oleandomycin in 125 ml. of methanol, after stirring at room temperature overnight, is treated with 21.2 g. of ammonium acetate. The resulting solution is cooled in an ice bath and treated with 1.26 g. of sodium cyanoborohydride. The cooling bath is then removed and the reaction mixture allowed to stir at room temperature for 2 hrs. The reaction is poured into 600 ml. of water and 600 ml. of diethyl ether and the pH adjusted from 8.3 to 7.5. The ether layer is separated and the aqueous extracted with ethyl acetate. The extracts are set aside and the pH of the aqueous adjusted to 8.25. The diethyl ether and ethyl acetate extracts made at this pH are also set aside, and the pH raised to 9.9. The diethyl ether and ethyl acetate extracts at this pH are combined, washed successively with water (1x) and a saturated brine solution and dried over sodium sulfate. The latter extracts, taken at pH 9.9, are concentrated to a foam and chromatographed on 160 g. of silica gel, using chloroform as the loading solvent and initial eluate. After eleven fraction, which amounts to 12 ml. per fraction, are taken, the eluate is changed to 5% methanol - 95% chloroform. At fraction 370 the eluate is changed to 10% methanol - 90% chloroform and at fraction 440, 15% methanol - 85% chloroform is used. Fractions 85–260 are combined and concentrated in vacuo to dryness to provide 2.44 g. of the desired product.

NMR (δ, CDCl₃): 5.56 (1H)m, 3.36 (3H)s, 2.9 (2H)m and 2.26 (6H)s.

What is claimed is:

1. A compound selected from the group consisting of:

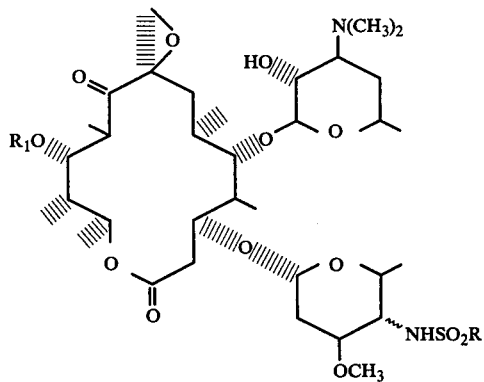

and a pharmaceutically acceptable acid addition salt thereof, wherein R is selected from the group consisting of alkyl having from one to three carbon atoms; 1,1,1-trifluoroethyl; phenyl; monosubstituted phenyl wherein said substituent is selected from the group consisting of fluoro, chloro, bromo, iodo, hydroxy, methoxy, cyano, carboxamido, nitro, amino, carbomethoxy, carbobenzyloxy, carboxy, trifluoromethyl, alkyl having from one to four carbon atoms and acetamido; disubstituted phenyl wherein said substituents are each selected from the group consisting of chloro, nitro, amino, methoxy and methyl; trichlorophenyl; hydroxy-dichlorophenyl; benzyl; naphthyl; thienyl; chlorothienyl; pyridyl; 2-acetamido-5-thiazolyl; 2-acetamido-4-methyl-5-thiazolyl; 2-benzimidazolyl; dimethyl-2-pyrimidinyl; pyrryl; furyl; substituted thienyl, pyrryl and furyl wherein said substituent is selected from the group consisting of carbomethoxy and alkyl having one to two carbon atoms; and 1-methyl-5-carbomethoxy-3-pyrryl; and R₁ is alkanoyl having from two to three carbon atoms.

2. A compound of claim 1 wherein R is thienyl.

3. The compound of claim 2 wherein R is 2-thienyl and R₁ is acetyl.

4. The compound of claim 2 wherein R is 3-thienyl and R₁ is acetyl.

5. A compound of claim 1 wherein R is substituted thienyl and R₁ is acetyl.

6. The compound of claim 5 wherein R is 3-methyl-2-thienyl.

7. A compound selected from the group consisting of:

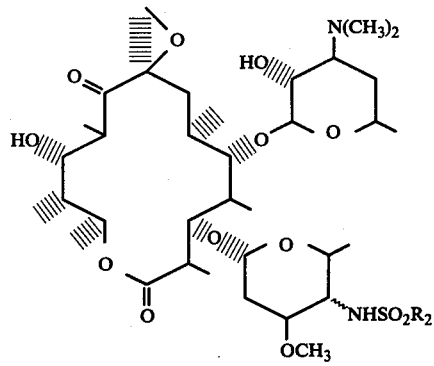

and a pharmaceutically acceptable acid addition salt thereof, wherein R₂ is selected from the group consisting of phenyl; substituted phenyl wherein said substituent is selected from the group consisting of chloro, fluoro, methyl, methoxy and trifluoromethyl; thienyl; and alkyl substituted thienyl said alkyl having from one to two carbon atoms.

8. A compound of claim 7 wherein R₂ is said substituted phenyl.

9. The compound of claim 8 wherein R₂ is 4-chlorophenyl.

10. A compound of claim 7 wherein R₂ is thienyl.

11. A compound of claim 10 wherein R₂ is 2-thienyl.

12. The compound of claim 10 wherein R₂ is 3-thienyl.

13. A compound according to claim 7 wherein R₂ is alkyl substituted thienyl.

14. The compound of claim 13 wherein R₂ is 3-methyl-2-thienyl.

15. A compound selected from the group consisting of:

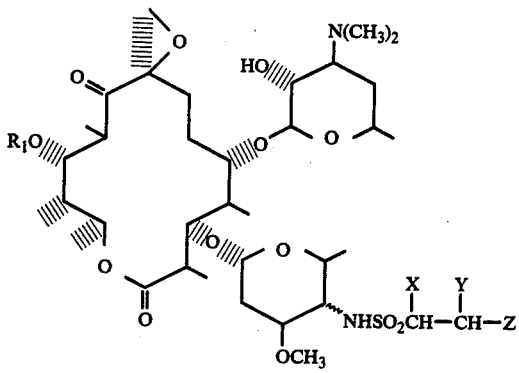

and a pharmaceutically acceptable acid addition salt thereof, wherein $R_1$ is alkanoyl having from two to three carbon atoms; X and Y when considered separately are each hydrogen; X and Y when considered together represent a carbon-carbon bond; and Z is selected from the group consisting of hydrogen, bromo, dialkylamino, said alkyl having one to three carbon atoms, alkylthio, said alkyl having one to three carbon atoms, phenylthio, 2-hydroxyethylthio and 1-morpholino, with the proviso that when X and Y represent a carbon-carbon bond, Z is hydrogen.

16. A compound of claim 15 wherein X and Y are each hydrogen and $R_1$ is acetyl.

17. The compound of claim 16 wherein Z is bromo.

18. The compound of claim 16 wherein Z is methylthio.

19. The compound of claim 15 wherein X and Y are a carbon-carbon bond and Z is hydrogen.

* * * * *